United States Patent [19]
Watanabe et al.

[11] Patent Number: 5,874,664
[45] Date of Patent: Feb. 23, 1999

[54] AIR FUEL RATIO SENSOR AND METHOD FOR ASSEMBLING THE SAME

[75] Inventors: Isao Watanabe, Nagoya; Michihiro Yamakawa, Kariya; Masanori Fukutani, Nagoya; Toshihiro Sakawa, Toyohashi; Nobuyuki Tsuji, Nukata; Minoru Ohta, Okazaki, all of Japan

[73] Assignee: Denso Corporation, Japan

[21] Appl. No.: 787,016

[22] Filed: Jan. 29, 1997

[30] Foreign Application Priority Data

Jan. 30, 1996 [JP] Japan .................................... 8-037448
Jan. 30, 1996 [JP] Japan .................................... 8-037449
Feb. 23, 1996 [JP] Japan .................................... 8-062165

[51] Int. Cl.$^6$ ........................... G01N 27/00; G01M 15/00
[52] U.S. Cl. .............................................. 73/23.32
[58] Field of Search ................. 73/116, 117.2, 73/117.3, 118.1, 23.31, 23.32; 60/276, 277

[56] References Cited

U.S. PATENT DOCUMENTS 5,490,412  2/1996  Duce et al. ............................. 73/118.1

FOREIGN PATENT DOCUMENTS 62-134061  2/1986  Japan .
61-25309   6/1986  Japan .
2-19726    5/1990  Japan .
6-229976   8/1994  Japan .

*Primary Examiner*—George M. Dombroske
*Attorney, Agent, or Firm*—Cushman Darby & Cushman Intellectual Property of Group of Pillsbury Madison & Sutro, LLP

[57] ABSTRACT

Air fuel ratio sensor for use in an exhaust gas purification system for an internal combustion engine. The sensor has an outer and inner cover 12 and 13 for protection of lead wires 16, 18 and 19 to a detecting element 3 and a heater 5 of the sensor, a rubber seal for 2 for obtaining a sealing between the covers and the lead wires and a water repellent filter 36 for obtaining a seal between the inner and outer covers 12 and 13, while keeping an air ventilation capability of the space inside the covers. For receiving the lead wires 16, 18 and 19, the seal 2 is formed with holes 20such that the minimum thickness between the holes and the minimum thickness between the hole and an outer surface of the seal is 1 mm or more. A crimping of the outer cover 12 is done so that a deformation of the seal 2 in a range between 10 to 20% of the outer diameter is obtained.

A crimping of the outer cover 12 is further done at a first section 12A at a larger force for fixation of the outer cover 12 to the inner cover 12 and at a second section 12B at a smaller force for holding the water repellent filter 36 between the outer and inner covers. In the crimping, the crimping at the first section is completed simultaneously or earlier from the completion of the crimping at the second section.

24 Claims, 17 Drawing Sheets

AIR FUEL RATIO SENSOR AND METHOD FOR ASSEMBLING THE SAME

BACKGROUND OF THE INVENTION

1. Field of the Invention

The present invention relates to an air fuel ratio sensor used for an air fuel ratio control in an internal combustion engine and a method for assembling the same and, in particular, crimping an outer cover.

Definition: The term "crimping force or crimping strength" in this specification means a rotating force applied to an outer cover connected to an inner cover by crimping, which causes the outer cover to commence its rotating movement with respect to the inner cover.

2. Description of Related Art

Known in a prior art is an air fuel ratio sensor arranged in an exhaust system of an internal combustion engine for detecting an air fuel ratio of an exhaust gas, which includes a housing, a detecting element in the housing, a protection cover arranged on an upper end of the housing, lead wires stored in the cover and an electric insulating member made with an elasticity and having holes for allowing the lead wires to pass through the holes, which lead wires are sealingly engaged with the respective holes by crimping the cover radially inwardly (Japanese Unexamined Utility Model Publication No. 2-19726).

This type of the sensor is for controlling a combustion control of the internal combustion engine. Namely, the air fuel ratio sensor detects an air fuel ratio of the exhaust gas, and the combustion control is done in accordance with the detected air fuel ratio, so that a three way catalytic converter can operate at an elevated efficiency in a purification of the exhaust gas. In order to detect the air fuel ratio, the detecting element is constructed by an oxygen ion conductive solid electrolyte body, which responds to the difference in an oxygen concentration between the exhaust gas and a reference gas in a reference gas chamber. Thus, a casing is formed with an air passageway for introduction of atmospheric air as the reference gas into the reference gas chamber. In order to prevent a water from being introduced into the air introducing passageway, a filter with air permeability and water repellency is arranged in the passageway (Japanese Unexamined Patent Publication No. 6-229976).

In the air fuel ratio sensor in Japanese Unexamined Patent Publication No. 6-229976, the protection cover assembly is constructed by an inner and outer covers as separate members, and the water repellent filter is arranged between the inner and outer covers. Furthermore, at the top, the inner and outer covers are formed with opening to which a rubber seal member is fitted, through which seal member, lead wires from the detecting element and the heater are taken out. The seal member functions to fix the lead wires and to prevent water from being leaked into the space inside the cover. Finally, the inner and outer covers are connected with each other by crimping at locations (three locations) corresponding to the water repellent filter and the rubber seal, respectively. In this way, the fixation of the inner and outer cover as well as the fixation of the water repellent filter and the rubber seal are done simultaneously.

It has recently been very usual that the air fuel ratio sensor is attached to an exhaust manifold adjacent the engine body. In view of the recent strong restriction of a discharge toxic components in the exhaust gas, such as OBD-II, LEV and ULEV, it is a recent trend that the air fuel ratio sensor is attached to an exhaust pipe located downstream from the three way catalytic converter. However, in comparison with the location adjacent the exhaust manifold, the position of the exhaust pipe downstream from the catalytic converter is likely to be subjected to water, thereby increasing a chance that water is introduced into a space inside the sensor.

In order to combat the latter problem, the Japanese Examined Patent Publication 61-25309 discloses an arrangement in an air introduction passageway for a filter provided not only with an air permeability but also with a water repellency. In this prior art, the air permeable and water repellent filter is arranged between the inner and outer covers. Furthermore, a rubber seal of tubular shape is arranged between the water repellent filter and the outer cover. A crimping of the outer cover is done so that a fixation of the filter together with the rubber seal member is done. This arrangement is capable of preventing the water repellent filter from being deformed. Furthermore, a fixation of the water repellent filter is done without causing its position to be dislocated. Furthermore, a water seal structure in the air introduction passageway is obtained by the rubber seal member.

The arrangement of the air fuel ratio sensor at the location downstream from the catalytic converter likely causes the sensor to be subjected to splashing with water by the rotating wheels of the vehicle, thereby causing the water to be introduced into the space inside the sensor. This causes the output level of the sensor to be reduced and causes a crack to be generated in a detecting element, resulting in damage in the sensor.

Furthermore, it is recently usual that the air fuel ratio sensor is provided with multiple lead wires due to an employment of a sensor with a heater or an employment of a laminated two cell type sensor. In this case, the rubber seal member must necessarily be provided with a large number of the holes for the lead wires. Thus provision of the large number of the holes in the seal member of a limited diameter causes thin portions to be created in the seal member at portions located between the lead wire holes and an outer surface of the member. The crimping of the cover after fitting the rubber seal with the lead wires causes a resulting compression force to be concentrated at the thin portion, thereby generating a large deformation. These portions of a large deformation may likely generate permanently deformed portions, when the rubber seal member is subjected to an atmosphere (exhaust gas) at a high temperature during the use of the sensor in an automobile. In this case, a sealing capacity is worsened between the lead wires and the corresponding holes, thereby reducing its waterproofness. Finally, under the recent trend of the location of the air fuel ratio at an environment of an increased temperature and of an increased chance of to an exposure to water, the structure of the air fuel ratio sensor in the prior art likely causes the waterproofness to be easily worsened.

As far as the structure of the air fuel ratio sensor in Japanese Unexamined Patent Publication No. 6-229976, the fixation of the rubber seal member as well as the fixation of the inner and outer covers are done by a single crimping operation. However, the outer cover is made heat resistant while the seal member is made from a different material such as a rubber. Thus, the simultaneous crimping operation may cause a desired crimped condition not to be obtained for both of the metal part and the rubber part. Namely, even if the crimping of the outer cover is desirably done, the undesirably crimped condition at the rubber seal member causes a water to leak via the gap between the rubber material and the inner cover. Contrary to this, if the rubber member is overly subjected to the crimping, it causes a crack to be generated in the rubber material. In this connection, an insufficient crimping implies a situation that the force during the crimping is not enough so that a deformation of the outer cover is smaller than a desired value. Contrary to this, an excessive crimping implies a situation that the force during the crimping is excessive so that a deformation of the outer cover is larger than a desired value.

Contrary to this, even if a desired crimped condition is obtained in the rubber seal member, an insufficient crimping of the outer cover to the inner cover may generate a situation that a water is leaked via the gap between the covers. Furthermore, if an excessive crimping is occurred between the inner and outer cover, a situation may occur that a crack is generated in the cover, which causes the material to be easily eroded.

Furthermore, it is usual that the rubber seal is located at the upper end of the sensor, while water repellent filter is located just below the rubber seal member. Thus, a situation may occur that, between the inner and outer covers, the fixation by the crimping is done only at the upper end of the sensor. In this case, the durability of the crimped portion between the inner and outer cover is insufficient to resist a vibration, which may cause the crimped portion to be loosened. This is disadvantageous in an arrangement of the air fuel ratio sensor at the location downstream from the catalytic converter, since this location is likely subjected to splashing by water as well as to a large vibration during the running of the vehicle.

In order to obviate the problem of the loosening at the crimped portion, a separate part maybe employed for preventing the parts from being loosened. However, this increase a work for an assembly of the sensor and a production cost is increased.

SUMMARY OF THE INVENTION

A first object of the present invention is to provide a air fuel ratio sensor capable of firmly securing lead wires in respective holes in an elastic seal member, while keeping a desired waterproofness and capable of used at an area of an increased temperature.

A second object of the present invention is to provide an air fuel ratio sensor capable of obtaining a desired durability and waterproofness, when used at a water laden or high temperature location.

A third object of the present invention is to provide a method for assembling the air fuel ratio sensor having a water repellent filter of a desired waterproofness and air ventilation capability, capable of reducing a number of parts, while an assembly is reliable and easy.

In order to attain the first object, the air fuel ratio sensor according to present invention has a construction as claimed in claim 1. The minimum thickness smaller than 1 mm may generate a permanent distortion by compression at an area of large compression stress when the sensor is used at a high temperature circumstance, resulting in the seal to be worsened between the lead wires and the holes, thereby reducing a waterproofness.

Contrary to this, the minimum thickness larger than 3.0 mm may obtain a desired waterproofness. However, the size of the seal member is increased, which cause a production cost to be increased due to the increased use of the rubber material. Furthermore, the size of the air fuel ratio sensor as well as related parts are correspondingly increased, resulting in an increase in cost due to increased use of materials. Furthermore, a productivity during an assembly of the sensor is worsened.

The deformation of the seal member smaller than 10% may cause the compression force to be insufficient in the seal member, which makes the seal to be insufficient between the lead wires and the corresponding holes. Contrary to this, the deformation of the seal member larger than 20% may cause the compression force to be excessive in the seal member, resulting in a generation of a defects such as a crack in the seal member.

The lead wires are, for example, for taking out a detecting signal from the detecting element, including a ground line as well as an electric supply to the heater, which number may be a single or plural.

Finally, the lead wire insertion hole may be singular or plural and may extend in parallel along the axis of the elastic seal member from its top to bottom ends.

According to the present invention, the minimum thickness between the lead wire holes and the minimum thickness between the outer surface of the seal member and the hole are both 1 mm or more. As a result, a desired reduction in the compression force is obtained at areas of a small thickness in the seal member. Thus, a reduction of a permanent distortion by compression is obtained at the small thickness areas under high temperature circumstances.

Thus, according to present invention, the lead wires are held in the corresponding holes under a stable and positive manner. As a result, when the sensor is subjected to a water, the sensor is prevented from being filled with water.

In order to obtain the deformation of the seal member in the range of 10 to 20% of the outer diameter, the seal member is subjected to a radially inward deformation. As a result, a desired compression force is generated in the seal member, thereby obtaining a desired sealed fixation of the lead wires in the corresponding holes in the seal member. Furthermore, a desired waterproofness is obtained even in the use of the sensor in a high temperature atmosphere. In other words, the sensor according to present invention can be used at a location of an internal combustion engine subjected to a high temperature, which was impossible in the prior art structure. Namely, the sensor according to present invention can be located not only at a position directly downstream from an exhaust pipe but also at a location in a casing of a three way catalytic converter. Thus, according to present invention a degree of the freedom as to the location of the air fuel ratio sensor is increased over the prior art structure, which makes it easy for the system to meet the recent severe restriction as to the exhaust gas.

In short, according to the air fuel ratio sensor in claim 1, a stable and positive fixation of the lead wires in the respective holes are realized, resulting in an increased waterproofness, while allowing the sensor to be used at a circumstance of an increased temperature.

In the invention in claim 2, the elastic seal member has hardness (Shore hardness) in a range 60 to 85 Hs, while being made of a rubber based on a fluorine. Thus use of this rubber allows the lead wires to be fixed in the corresponding holes in a more reliable manner, thereby enhancing the service life under high temperature circumstances. The rubber of the hardness more than 85 Hs may cause the seal member to be less flexible, thereby making it difficult to obtain a desired contact with respect to the lead wires. In the invention, the hardness of 60 Hs means the hardness of the fluorine polymer prior to the addition of a reinforcement agents.

The invention in claim 3 of the outer diameter larger than 8.5 mm with 3 to 5 holes makes the lead wire insertion holes to be distributed at a equal spacing, thereby obtaining a substantially uniform thickness of the material along the entire cross section of the seal member. Furthermore, the outer diameter of the seal member smaller than 8.5 mm makes it possible that the minimum thickness to be smaller than 1 mm.

It should be noted that the diameter of the lead wire insertion hole is the one which makes the lead wire to pass through, while the diameter of the lead wire is, generally, in a range of 1.6 to 2.3 mm from point of view of strength and cost.

The invention in claim 4 of the provision for ribs allows the ribs to be more easily deformed, thereby obtaining a desired seal between the lead wires and the corresponding holes, resulting in an increased waterproofness of the air fuel ratio sensor. Furthermore, the outer cover is subjected to a crimping at the locations of the ribs, so that a desired deformation of the ribs is obtained even in a situation that a large difference exists in the inner diameter of the lead wires insertion hole and the outer diameter of the lead wire, which may cause the ribs to be free from a deformation by a mere press fitting of the lead wires to the hole. Thus, a stable and positive seal is obtained between the lead wire and the corresponding opening.

In the embodiment, the ribs are constructed as a projection or projections at the inner wall of the holes. The projection may be an arc shaped or a triangle cross sectional shape.

In order to attain the second object, the invention in claim 5 provides an outer cover provided with a first section opposed with the inner cover with no intervention of the water repellent filter and a second section opposing with the inner cover via the water repellent filter. In the invention in claim 5, the fixation of the first and second cover is done by a crimping at a first location where no water repellent filter exists between the inner and outer covers. When the first section is located at a position adjacent the housing rather than a location at an upper end, i.e., a position nearer to the housing than the second section, an increased diameter at the crimped portion is obtained, thereby increasing the strength at the crimped portion. As a result, a desirable crimping is obtained between the inner and outer covers. In other words, the outer cover is, at the first section, desirably crimped to the inner cover, thereby enhancing a durability to a vibration. Thus, the covers are prevented from being easily loosened, resulting in an increased sealing performance at the second section. Furthermore, also at the second section, where the water repellent filter is provided, a loosening is prevented, thereby obtaining a desired sealing ability.

Furthermore, between an upper end of the inner cover and the outer cover, a member for obtaining an electrical insulation or for preventing lead wires from being withdrawn is held. For example, a stepped portion is formed between an upper end of the inner cover and the outer cover in order to hold the insulating member. By using the insulating member, a reliable insulation is obtained even in a situation that a plurality of lead wires are used, thereby obtaining an improved performance and a reliable operation of the air fuel ratio sensor. Otherwise, a construction for obtaining an electric insulation as well as for preventing the lead wires from being withdrawn would be complicated, resulting in an increase in work during an assembly, causing the production cost to be increased.

In short, in the invention in claim 5, an air fuel ratio sensor of desired vibration durability as well as waterproofness during a use in severe environmental conditions can be provided.

In the invention in claim 5, the water repellent filter may be made from a material having an air permeability as well as a water repellency, such as a porous material made of polytetrafluorethylene (PTFE). The inner and outer covers may be provided with openings for introduction of an atmospheric air so that the filter is located between the openings. Finally, the filter may be a tubular shape.

The construction of claim 7 of an increased diameter of the inner diameter at the first section over that in the second section is desirable for increasing a durability to a vibration, without causing its assembling to be difficult.

The construction of claim 8 of the outer cover having an upper opening sealed by a rubber seal is desirable for preventing an water from being introduced from the opening.

The construction of claim 9 of the increased hardness at least at the first section of the outer cover allows the latter to be neatly and positively fitted to the inner cover. Thus, the water repellent filter is positively held at a position between the inner and outer covers by the crimping, while preventing the position from being dislocated, resulting in an increase in a waterproofness.

The invention in claim 12 features that the inner and outer covers are made of stainless steel of values of hardness and wall thickness which are in respective ranges. The wall thickness of the inner cover smaller than 0.4 mm may cause the strength of the cover to be overly reduced, resulting in a possibility that a protection of parts by the cover can not be attained. Contrary to this, the wall thickness of the inner cover larger than 0.8 mm may causes the crimping to become difficult due to an increased crimping force. Furthermore, a generation of erosion is likely due to a crack generated by the force in the crimping during the use of the sensor.

In the invention in claim 12, The wall thickness of the outer cover smaller than 0.3 mm may cause the strength of the cover to be overly reduced, so that the cover is easily deformed and it may possible that a stable fixation of the outer cover to the inner cover can not be obtained. The wall thickness of the inner cover larger than 0.6 mm may causes the crimping to become difficult.

In the invention in claim 12, a similar determination is done as to the range of the hardness of the inner and outer covers.

In the invention in claim 13 of the circumferentially spaced 8 points of the crimping, an evenly distributed force is applied along the entire circumference of the inner and outer covers, so that a uniform deformation of the inner and outer covers is obtained along the entire circumference. Thus, an even fixation as well as a desired sealed condition are obtained between the inner and outer covers. Namely, the crimping operation is done by a crimping apparatus having circumferentially and evenly spaced eight pressers, which are moved radially inwardly. In other words, the same radially inwardly directed force is applied to each of diametrically opposite and circumferentially evenly spaced pair of the presser members, thereby maintaining a stable position of the members to be crimped during the crimping operation. Contrary to this, the crimping at six position may cause the spacing between the pressers to be excessively long in the circumferencial direction, resulting in an uneven crimping in the circumferencial direction, resulting in an insufficient sealing at the crimped portions. Furthermore, it may possible that the cross sectional shape of the cover is other than the desirable circular cross sectional shape. Finally, a crimping at seven positions will be impractical from the view point of a design of the apparatus. Furthermore, a crimping at points of nine or more makes the number of working steps during the crimping to increase due to the increased number of pressers, which requires an extra labor cost.

As to the second section of the outer cover, it is desirable that the crimping is done at 8 locations in a similar manner.

In order to attain the third object, the invention of claim 16 or 17 features that the crimping of the first section is finished prior to or faster than the finish of the crimping of the second section. The first section is the portion, which makes the outer cover to contact with the inner cover, while the second section is a portion where the water repellent filter of a soft nature is located. Thus, the strength of the crimping at the second section is less than that at the first section.

When the crimping of the first section continues later than the finish of the second section, a crimping force is still applied to the first section. The strength of the crimping at second section is smaller than that at the first section. Thus, the large crimping force at the first section, which is still continued, causes the inner and outer covers to be relatively moved in a direction parallel to the axis of the sensor or in a rotating direction about the same axis, resulting in the sealing to be worsened between the water repellent seal and the inner and outer covers.

Contrary to this, according to the invention, the crimping of the larger force at the first section is finished prior to or simultaneously with the finish of the crimping of the smaller force at the second section. In this case, the small crimping force at the second section does not influence the crimped state at the first section, thereby preventing the inner and outer covers from being mutually displaced. Thus, a desired and stable crimping is maintained between the inner and outer sections and water repellent filter, thereby obtaining a desired sealed condition.

According to the present invention, during the assembling of the water repellent filter, an additional part such as a rubber member is unnecessary, while keeping a desired sealed condition. Thus, a number of parts for the sensor is reduced. Furthermore, the number of working steps for assembling the parts are reduced, while keeping the desired sealing function. Furthermore, a reliable assembling of the parts becomes possible.

Finally, in the invention, the positional relationship between the first and second sections is not important. Namely, the first section can be located below the second section or vice versa.

In the invention in claim 18, the crimping of the first section without the intervention of the water repellent filter is subjected to initial stage crimping. As a result, a uniform radial spacing is obtained in a space between the inner and outer covers, in which the water repellent filter is arranged. The second stage crimping is then commenced, so that the water repellent filter is subjected to an uniform deformation along the entire circumference, causing the filter to be fixed between the inner and outer covers.

In the invention in claim 19, the crimping is done, while keeping the sensor to be horizontal, which makes it easy for an operator to monitor from the lateral sides if the crimping is properly done.

In the invention in claim 20, a rubber tube is arranged between the outer cover in the first section and the inner cover. This arrangement makes it possible that the lead wires are protected in a case where the first section is located above the second section.

In the invention in claim 21, the outer cover in the first section is in a direct contact with the inner cover. By this construction, an increased strength of the crimping at the first section is positively obtained while using a minimum number of parts.

In the invention in claim 22, at least the crimping of the first section is done at eight circumferentially spaced positions, which makes an uniformly distributed force to be applied to an entire circumference of the inner and outer covers, thereby uniformly deforming the covers at their entire circumference during the fixation by the crimping. Thus, a desired sealed condition is obtained at crimped portions between the inner and outer covers. This is because, during the crimping, presser members evenly press the work at opposite positions in each of vertical, horizontal and oblique directions. This effect of the invention in claim 21 is the same as explained with reference to the invention in claim 13.

The pressers of the crimping apparatus are advantageously of a sector shape having end operating surface as an arc matched to a circumferencial shape of the metal covers to be subjected to the crimping. Contrary to this, when the operating end forms a flat shape, the covers would form, in a transverse plane, a polygonal shape, which cause gaps to be likely generated at the portions corresponding to the corner of the polygonal shape. The employment of the arc shape of the operating surface can prevent such a difficult, thereby keeping a desired sealing capacity.

In the invention in claim 23, the inner cover has, at least at the first section, a hardness larger than that of the outer cover. By this construction, a fixation of the outer cover to the inner cover becomes possible without occurrence of any rattle. Thus, the water repellent filter is held between the cover without occurrence of its dislocation, thereby keeping a desired waterproofness.

In the invention in claim 24, the inner and outer covers are made of a stainless steel and have ranges of hardness Hv between 150 and 400 and between 100 and 300, respectively, while the hardness of the inner cover is, at least its first section, larger than that of the outer cover. This construction can make it possible to maintain a stable crimped condition even under a condition of a use of the sensor at a higher temperature.

A hardness of the inner cover smaller than 150 causes the difference with respect to the hardness of the outer cover to be excessively small, which causes the condition of the crimping to be worsened. Furthermore, the inner cover is likely to be deformed, which prevent the body of the sensor from being desirably protected. Contrary to this, a degree of the hardness of the inner cover larger than 400 can cause a crack to be generated during working. Furthermore, a stress erosion crack can be generated during use after the fixation. A degree of the hardness smaller than 100 can be almost below the limit which is practically produced and causes the strength to be small, so that a deformation may be generated by an outside force generated, for example, by stones thrown rotating wheels.

The degree of the hardness of the outer cover larger than 300 causes the difference thereof to be insufficient with respect to the degree of the hardness of the inner cover, which causes the crimping to be difficult, thereby causing the fixation to be insufficient.

In the invention in claim 25, the wall thickness of the inner cover is larger than that of the outer cover, which makes the strength of the inner cover to be larger than that of the outer cover. Thus, reliable crimping is obtained between the inner and outer covers and the water repellent filter.

In the invention in claim 26, the inner and outer covers are made from a stainless steel, the inner cover has a hardness Hv in a range between 150 and 400, the outer cover has a hardness Hv in a range between 100 and 300, the thickness of the inner cover is in a range between 0.4 and 0.8 mm, and the thickness of the outer cover is in a range between 0.3 and 0.6 mm. A thickness of the inner cover smaller than 0.4 mm causes its strength to be insufficient, resulting in deteriorating the designated function as the cover for protecting parts therein. Contrary to this, a thickness of the inner cover larger than 0.8 mm causes the working to be difficult, and a stress erosion crack can be generated during use after crimping. The thickness of the inner cover smaller than 0.4 mm causes its strength to be insufficient, resulting in deteriorating the designated function as the cover for protecting parts therein. A thickness of the outer cover smaller than 0.3 mm causes the strength to be insufficient, so that the deformation by an outer force is likely, and it is possible that the inner cover is not securely connected to the inner cover. The thickness of the outer cover larger than 0.6 mm may cause the crimping to be difficult.

A thickness of the inner cover smaller than 0.4 mm causes its strength to be insufficient, resulting in deteriorating the designated function as the cover for protecting parts therein. Contrary to this, a thickness of the inner cover larger than 0.8 mm causes the working to be difficult, and a stress erosion crack can be generated during use after crimping. The hardness of the inner and outer covers are determined under the similar consideration.

The invention in claim 27 features a crimping device including the first pressers which are operated first to crimp the first section and second pressers which are operated later to crimp the second section. Thus, a positive crimping operation is realized.

In the invention in claim 28, the section is crimped by the first pressers, and after the completion of the crimping, the crimping of the second section by the second pressers is done. Thus, the crimping at the first section is initially brought to the secured condition, which assures that the inner and outer covers for generating the space for the water repellent filter are concentric, thereby obtaining a stable crimping operation. The first and second pressers may be advantageously made separate, and independently operated.

In the invention in claim 29, after the commencement of the crimping of the first section by the first pressers, the crimping of the second section by the second pressers follows, and the crimping at the first and second section finish simultaneously. Thus, a number of working steps for executing the crimping is reduced. In this case, the crimping apparatus may be constructed such that the first and second pressers are made integral (FIG. 17).

In the invention in claim 30, the crimping at the first section is commenced earlier than the commencement of the crimping at the second section. In this case, the first section with no intervention of the water repellent filter is initially crimped. Thus, a substantially uniform radial spacing between the inner and outer covers for storing the water repellent filter is obtained. Then, the crimping of the second section where the water repellent filter is done in a radially inward direction. Thus, the water repellent filter is subjected to an uniform deformation along the entire circumference, thereby fixing the filter between the inner and outer covers. Thus, a reliable and secure fixation of the water repellent filter between the inner and outer covers is realized.

In this construction of the crimping method, the fixation of the water repellent filter is done without using a separate part such as a rubber member between the water repellent filter and the outer cover. Thus, a reduction in the number of parts in the oxygen concentration sensor is realized, and a reduction of the labor during the assembling is realized. Thus, in the invention in claim 29, a reduction of the number of parts is possible, while keeping the assembling process to be a reliable and easy.

In the invention in claim 29, the water repellent filter is, as in the invention in claim 15, made of PTFE. Furthermore, as in the invention in claim 15, air inlet holes are provided in the inner and outer covers for introduction of air. The water repellent filter is arranged so that it is interposed between the air induction holes. The water repellent filter may be of a tubular shape.

In the invention in claim 32, the inner and outer cover are in respective desired range of hardness. The advantage is the same as that of claim 24, i.e., a stable crimping operation is maintained in the case of use in an increased atmospheric temperature.

In the invention in claim 33, the crimping apparatus is comprised of first pressers which are initially operated for crimping the first section and second pressers which are then operated. Thus, the crimping of the first section at the initial crimping stage, which is followed by the crimping of the second section is easily realized.

In the invention in claim 34, after the completion of crimping by operating the first section by the first pressers, the operation of the second presser is commenced for crimping the second section. Thus, as in the invention in claim 28, a stable crimping can be obtained at the second section.

Finally in the invention in claim 35, the crimping by the first pressers started at the initial stage and the crimping by the second pressers stated later are completed simultaneously. Thus, a reduction is possible in the number of working steps for the crimping.

BRIEF EXPLANATION OF ATTACHED DRAWINGS

Figure 8A:
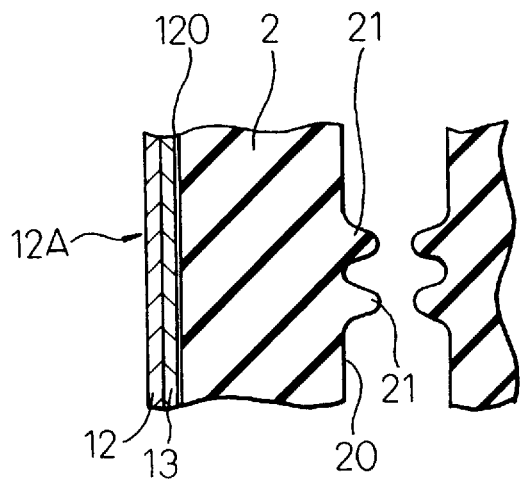
FIG. 8A is an enlarged partial cross sectional view of a lead wire insertion hole in the elastic seal member in FIG. 2.
Figure 8B:
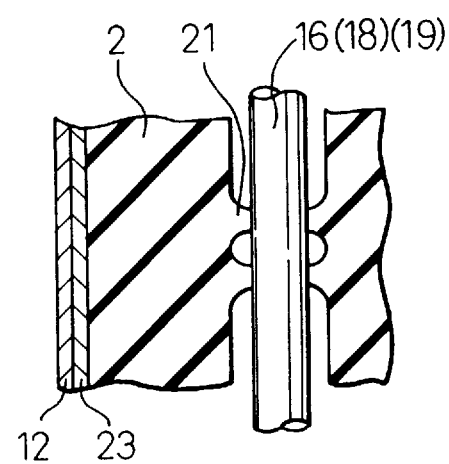
FIG. 8B is the same as FIG. 8A but shows a condition after a lead wire is inserted.
Figure 9A:
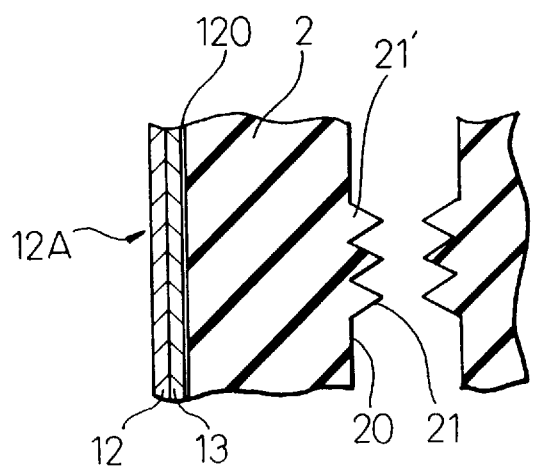
Figure 9B:
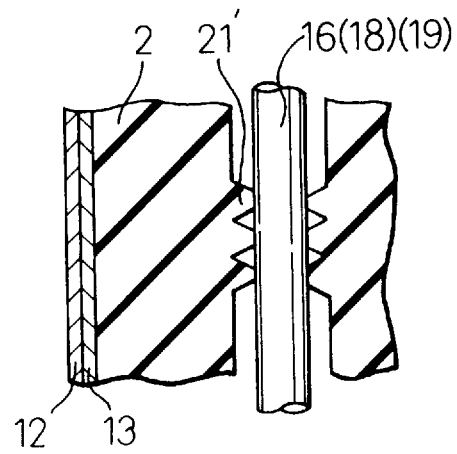

FIGS. 9A and 9B correspond to FIGS. 8A and 8B, respectively in a modification.

Figure 10:
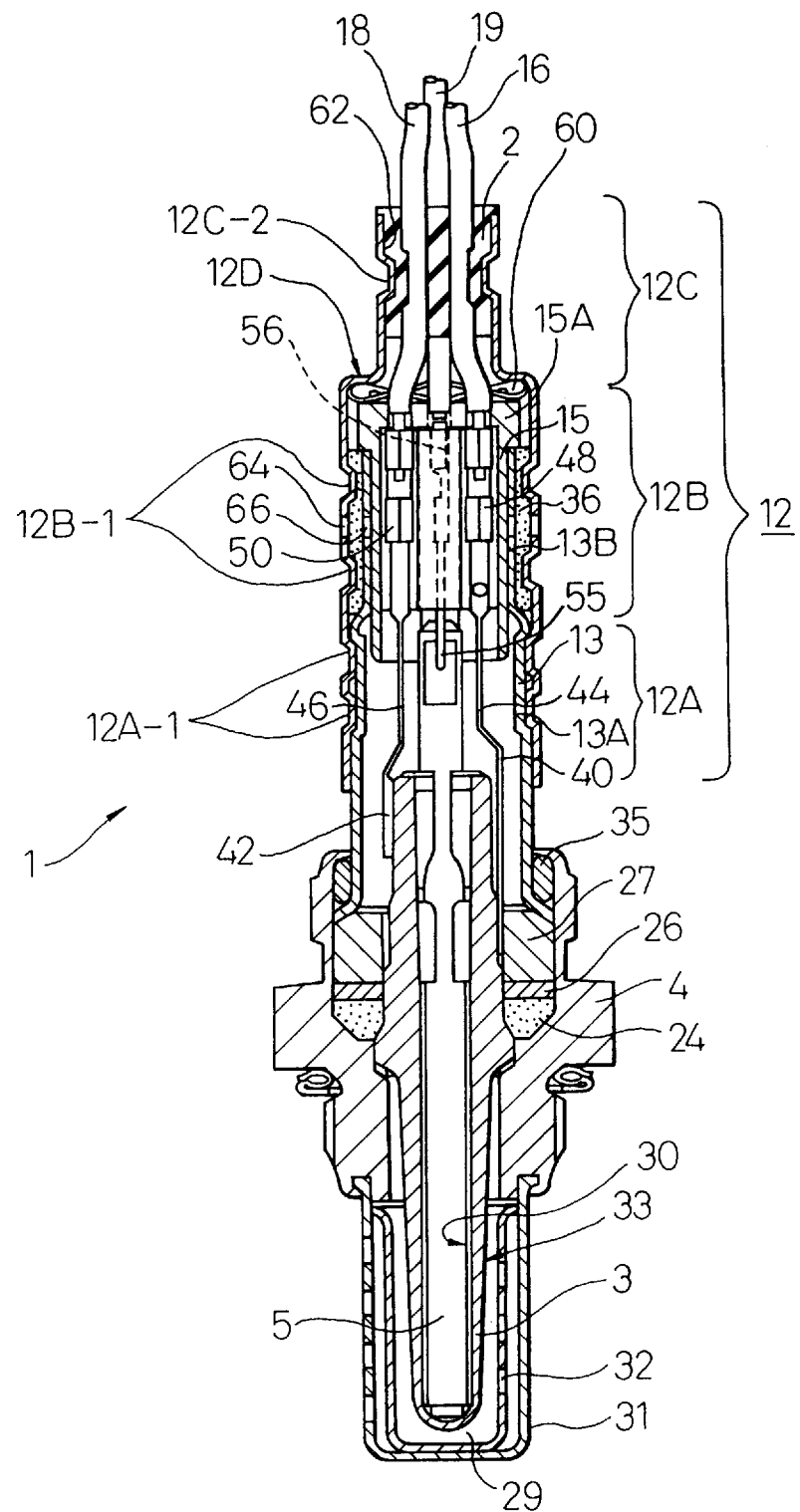

FIG. 10 is a longitudinal cross sectional view of an air fuel ratio sensor in a different embodiment.

Figure 11:
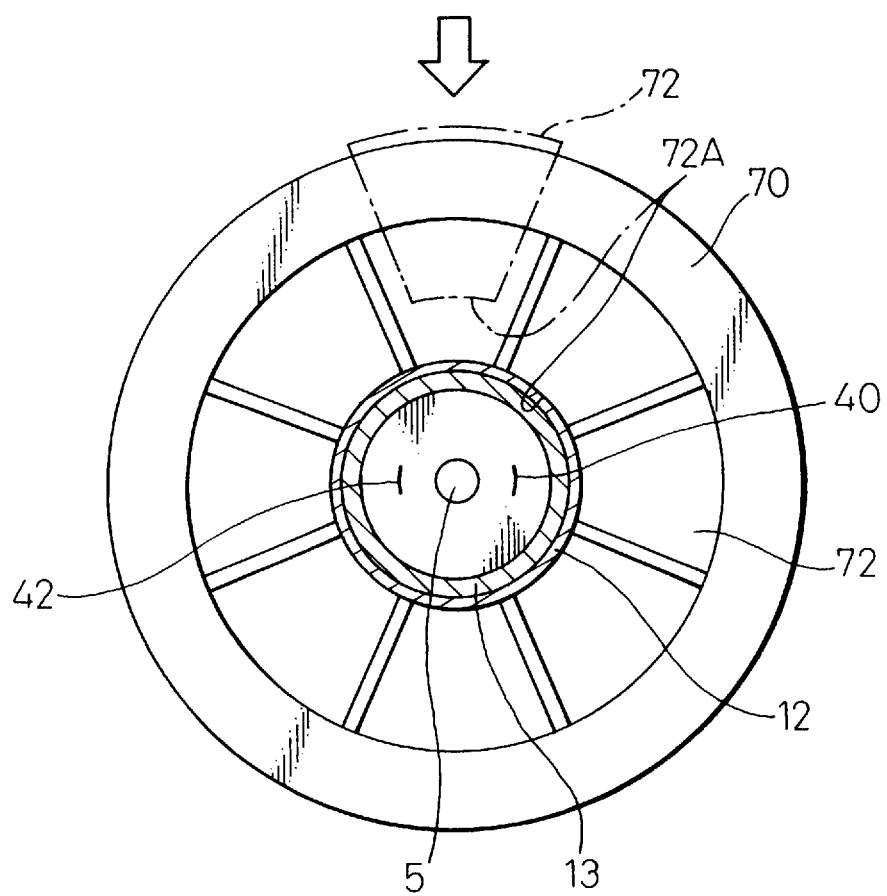

FIG. 11 shows a transverse cross sectional view of the sensor in FIG. 10 with a crimping apparatus.

Figure 12:
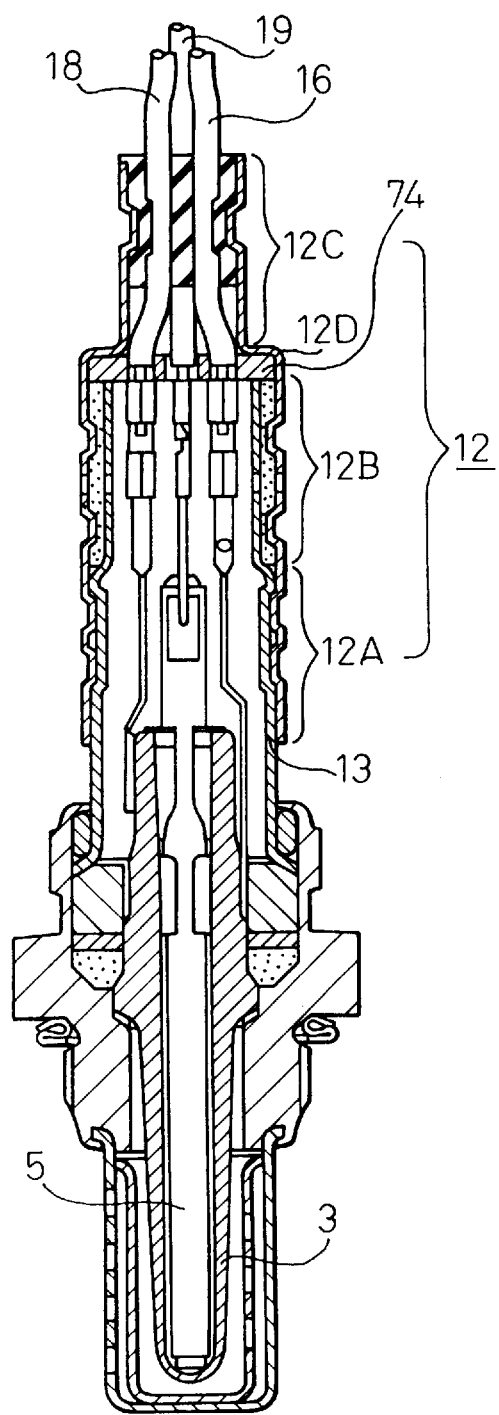

FIG. 12 is a longitudinal cross sectional view of an air fuel ratio sensor in another embodiment.

Figure 13:
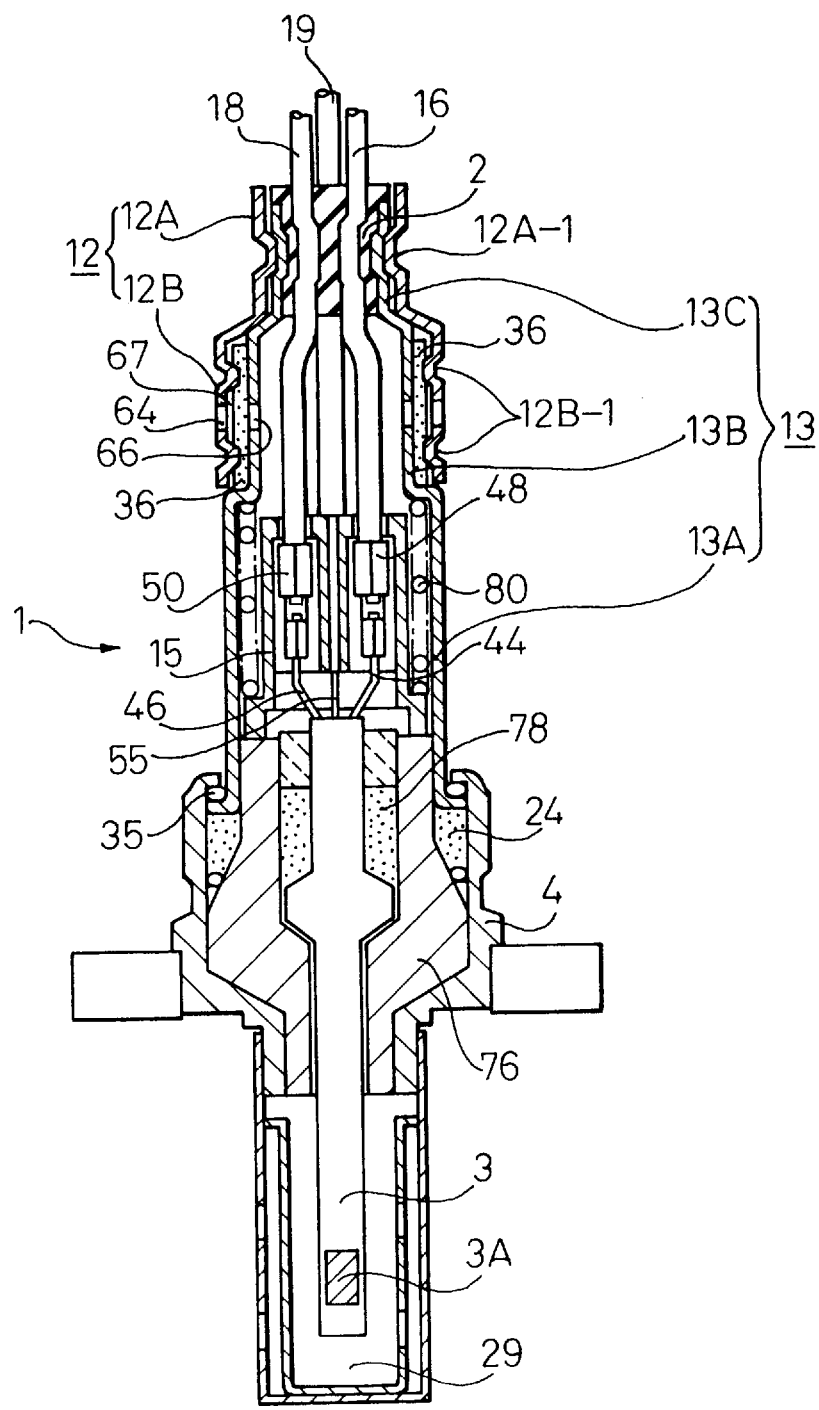

FIG. 13 is a longitudinal cross sectional view of an air fuel ratio sensor in a further another embodiment.

Figure 14:
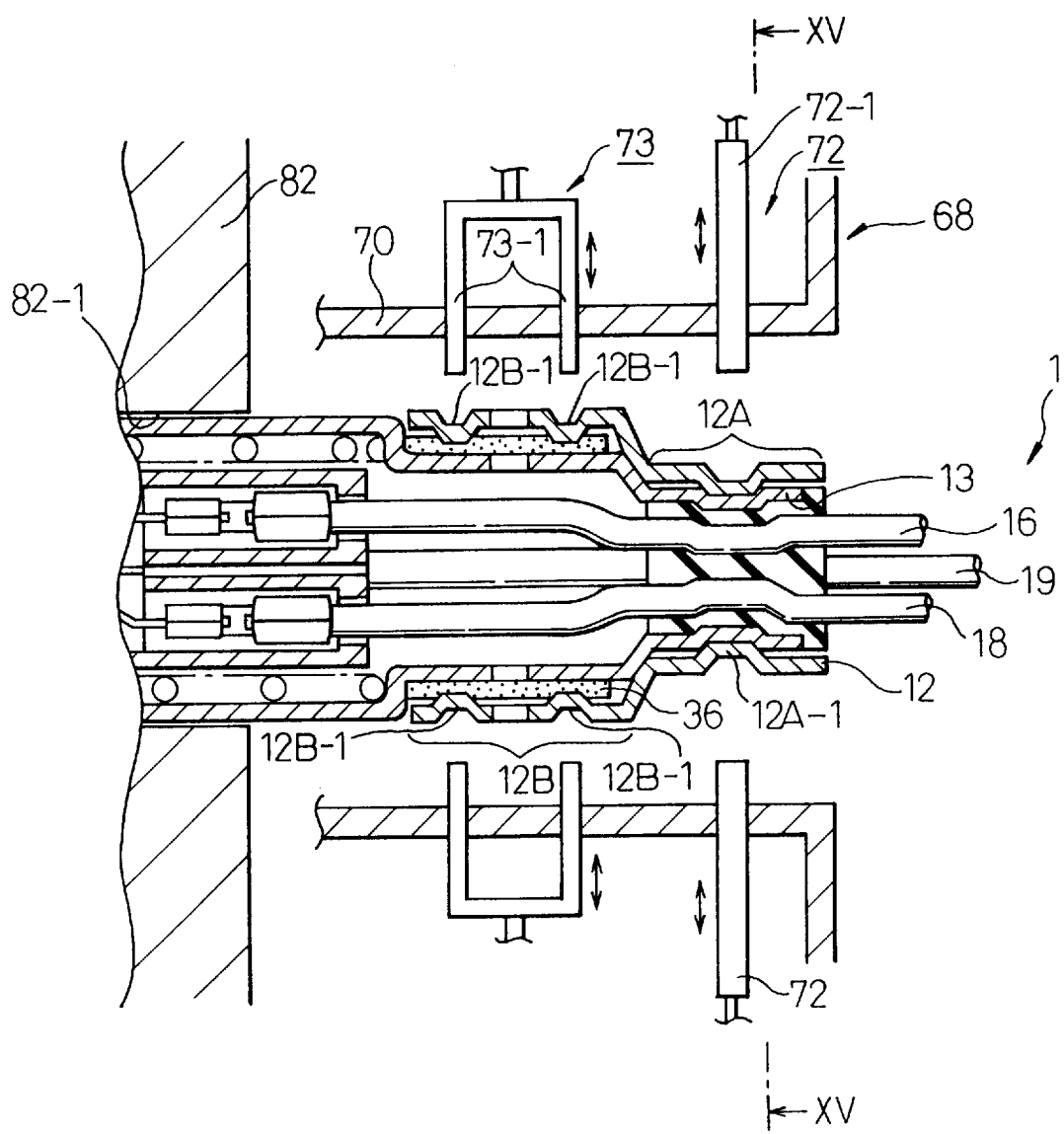

FIG. 14 shows a longitudinal cross sectional view of a crimping apparatus with the sensor in FIG. 13.

Figure 15:
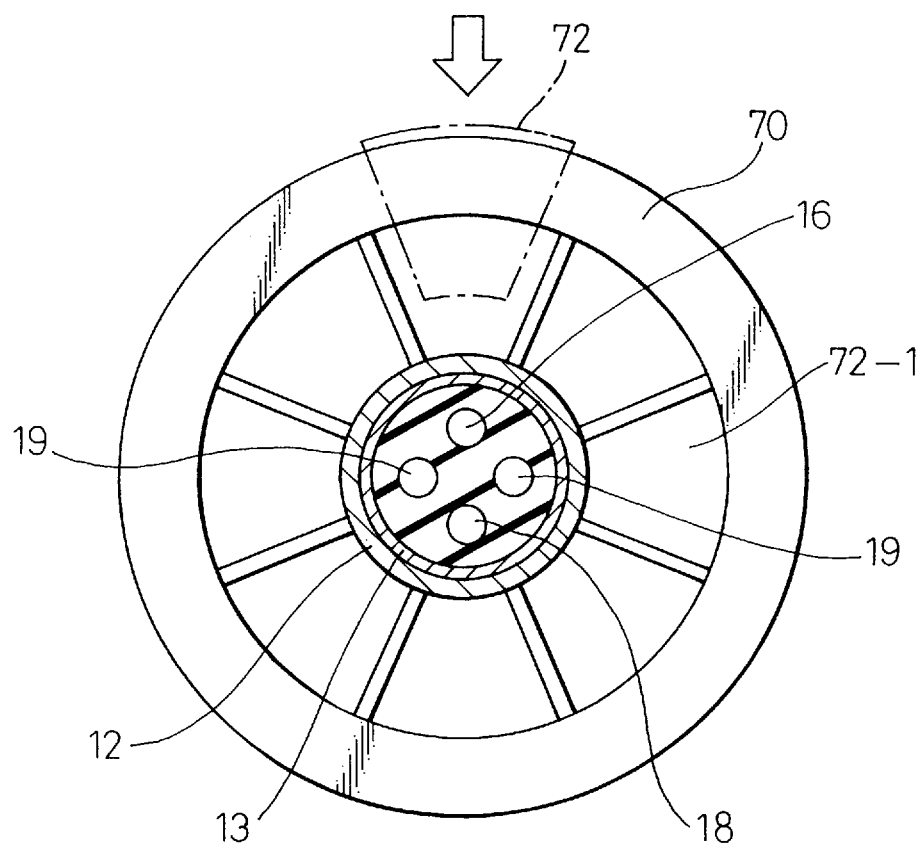

FIG. 15 is a transverse cross sectional view taken along lines XV—XV in FIG. 14.

Figure 16A:
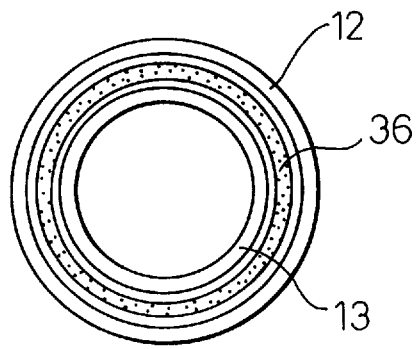

FIG. 16A shows a cross sectional view of the sensor after completion of the crimping according to the present invention.

Figure 16B:
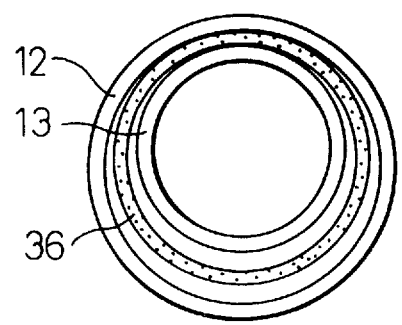

FIG. 16B shows a cross sectional view of the sensor after completion of the crimping in the prior art.

Figure 17:
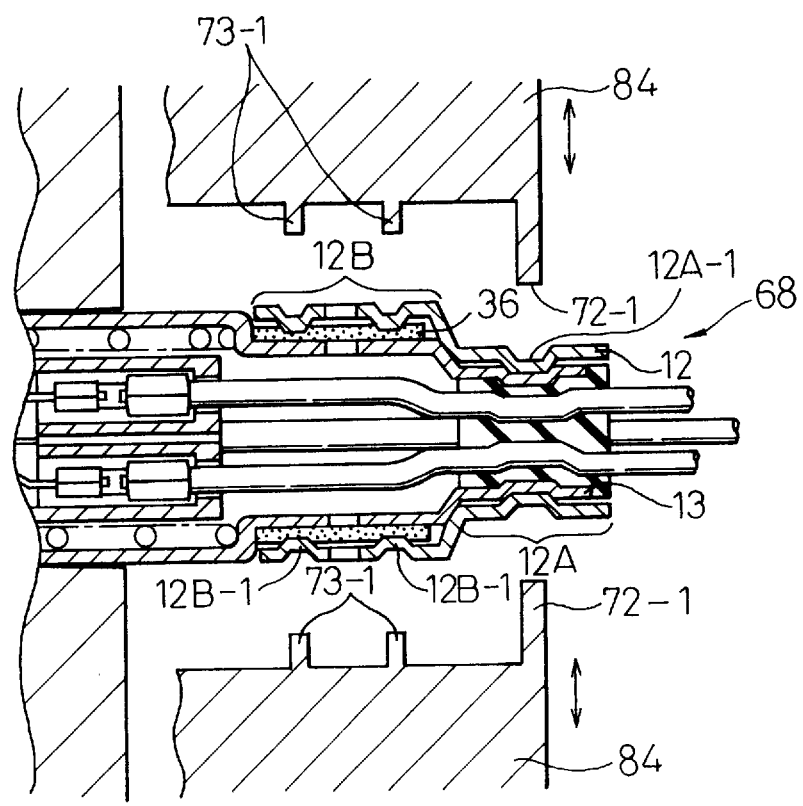

FIG. 17 shows a modification of the crimping apparatus according to the present invention.

Figure 18:
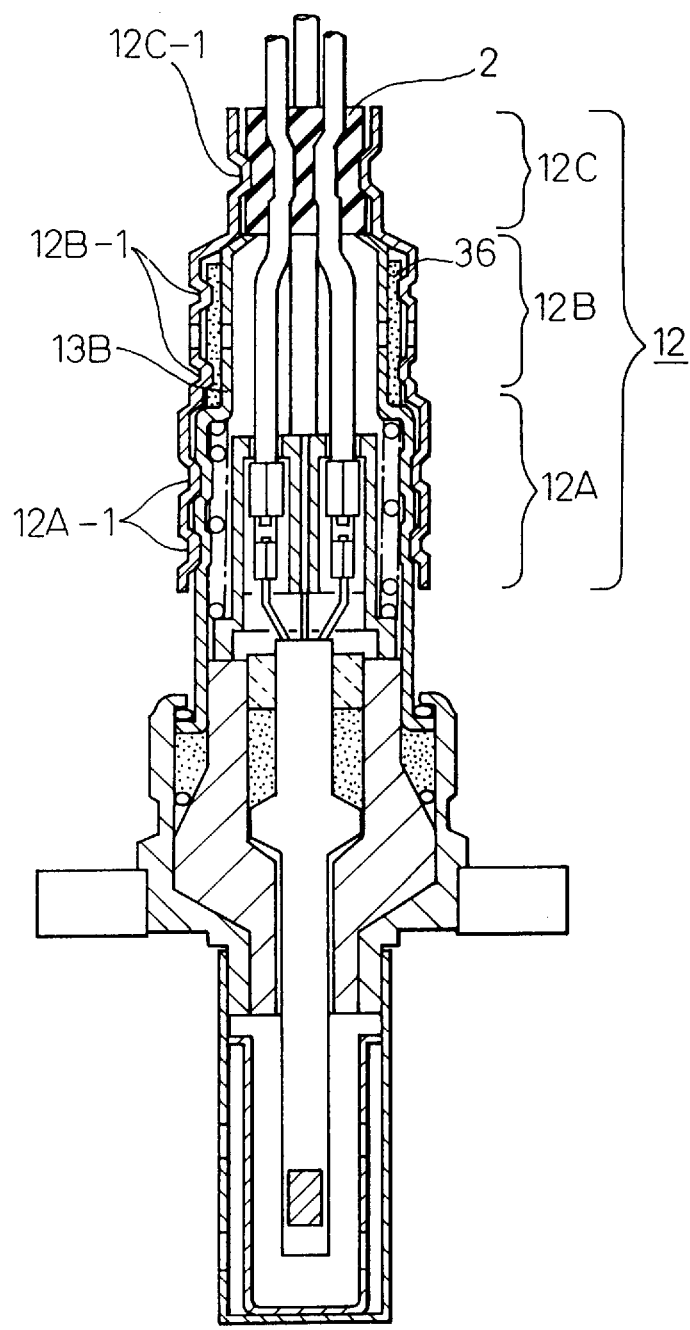
Figure 19:
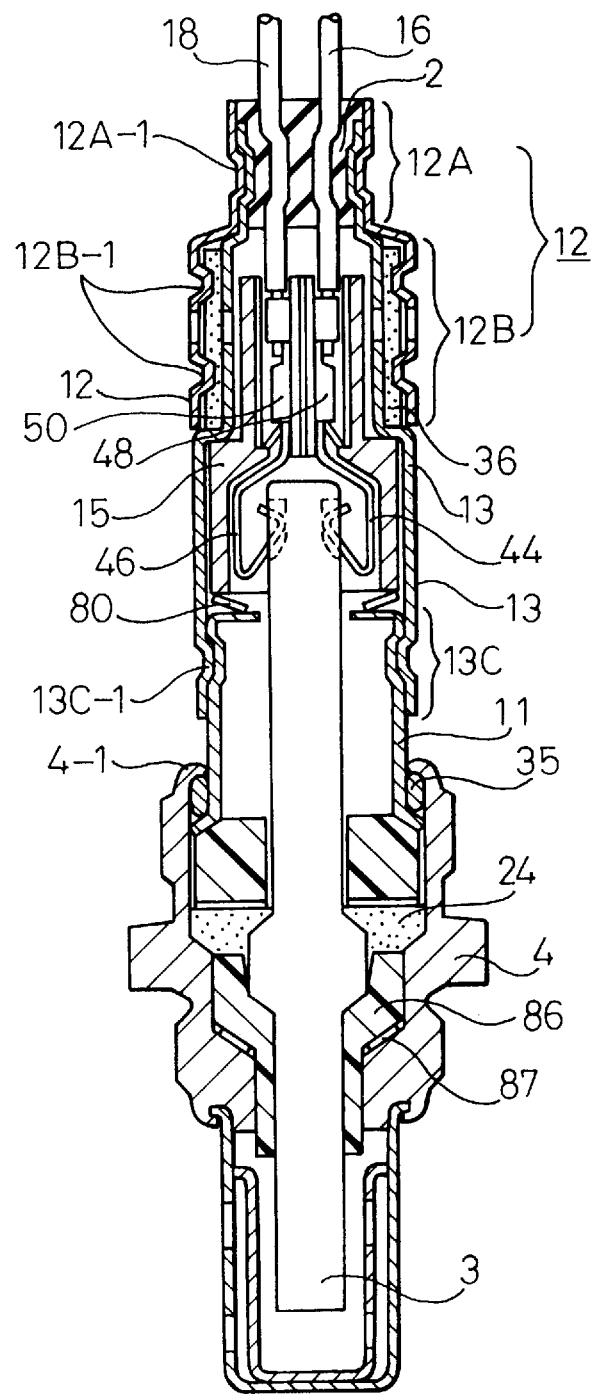

FIGS. 18 and 19 are longitudinal cross sectional view of air fuel ratio sensors in different embodiments, respectively.

Figure 20:
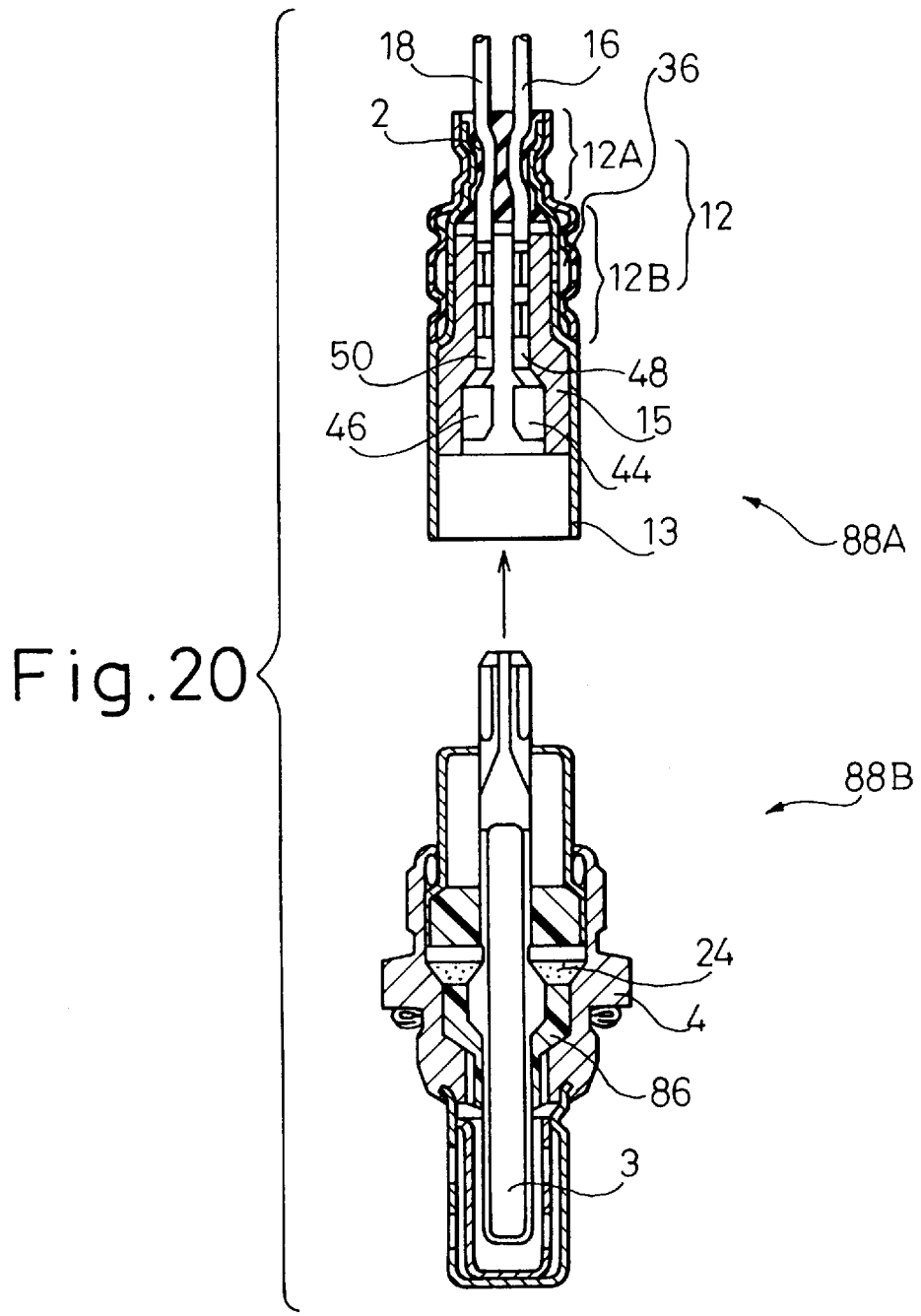

FIG. 20 shows sub-assemblies of the sensor in FIG. 19 before they are assembled.

Figure 21:
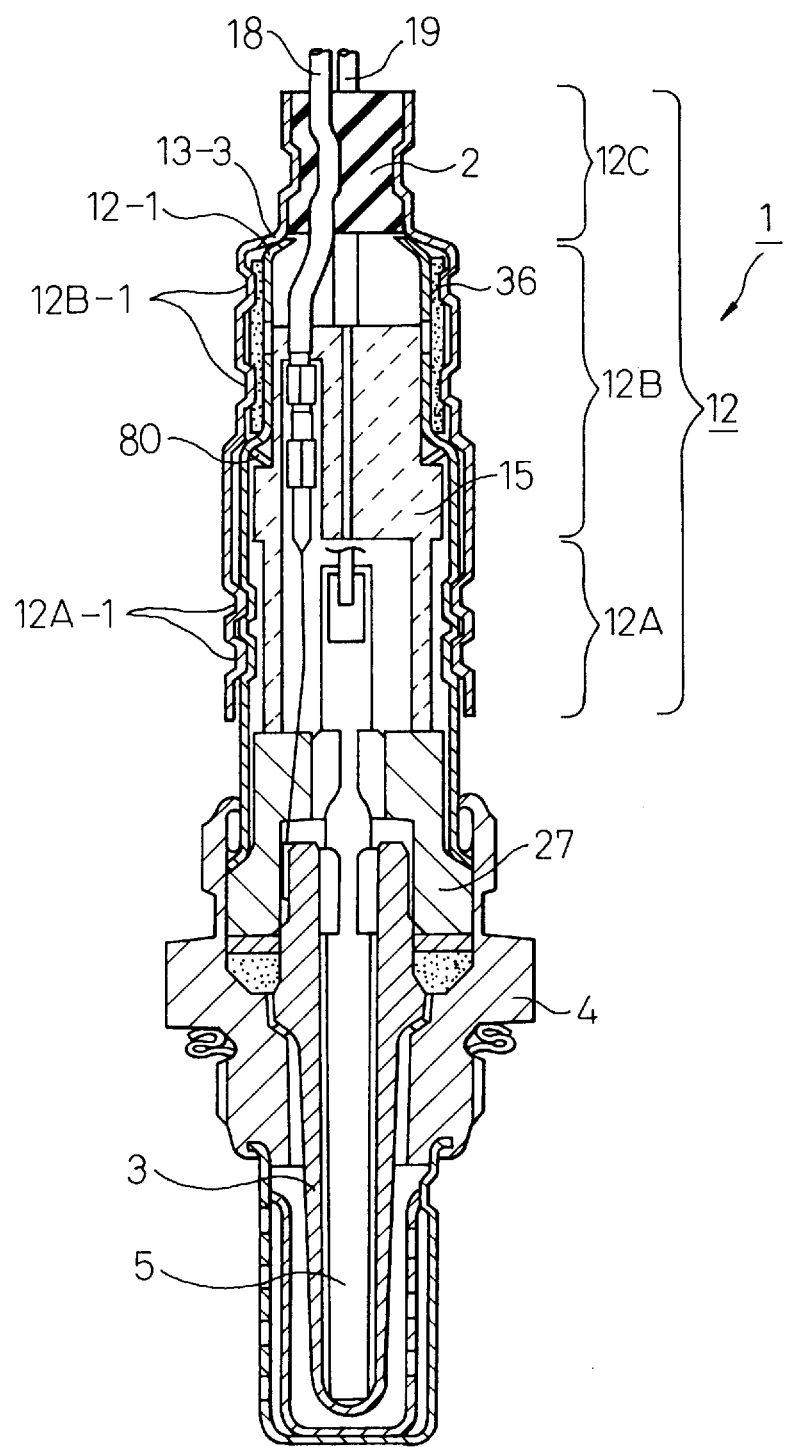
Figure 22:
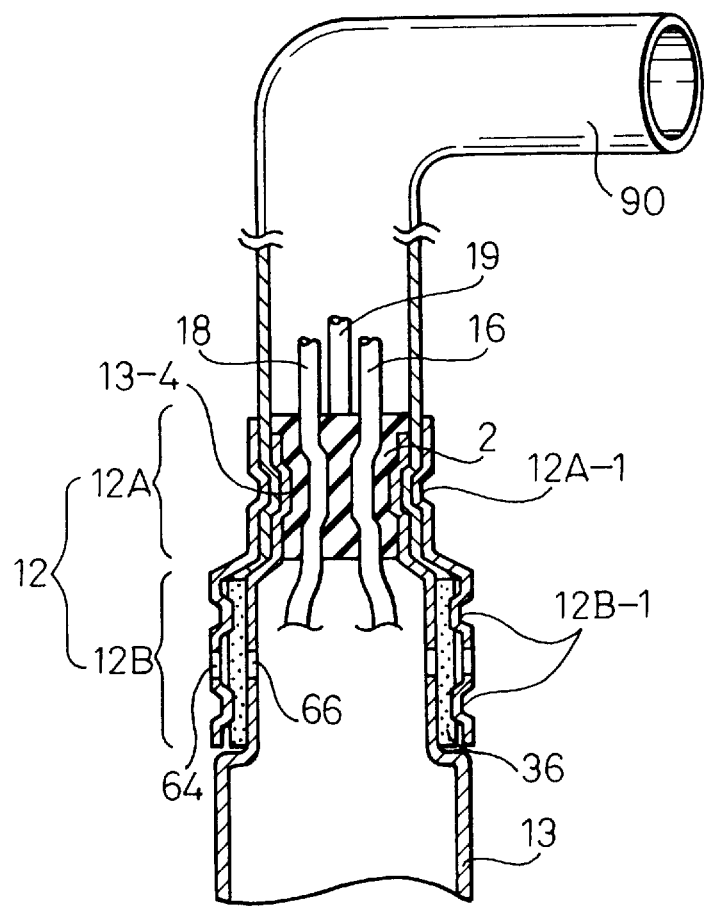

FIGS. 21 and 22 are longitudinal cross sectional view of air fuel ratio sensors in different embodiments, respectively.

DETAILED EXPLANATION OF PREFERRED EMBODIMENTS

Now, embodiments of the present inventions will be explained with reference to attached drawings.

In FIGS. 1 to 4 showing an embodiment of the present invention, an air fuel ratio sensor 1 includes a seal member 2 made of an elastic and electrically insulating material, such as a rubber, a detecting element 3, a housing 4 for storing therein the detecting element 3, a heater 5, a bottom (lower) cover 11, outer and inner covers 12 and 13, an inner electric insulator 15 made of a rigid insulating material such as a ceramic, and lead wires 16, 18 and 19 inserted to the covers 12 and 13. The elastic seal member 2 is arranged in the protection covers 12 and 13. Furthermore, the elastic seal member 2 is formed with holes 20 through which the lead wires 16, 18 and 19 are inserted, respectively.

Figure 2:
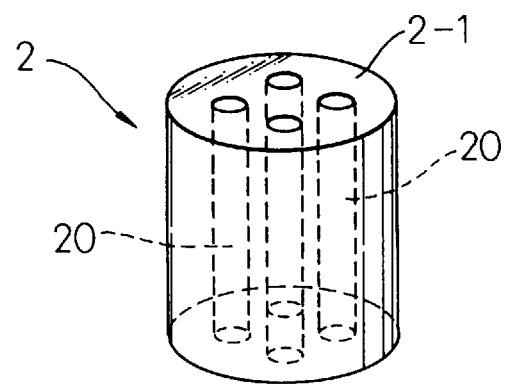
FIG. 2 is a perspective view of an elastic seal member in FIG. 1.
Figure 3:
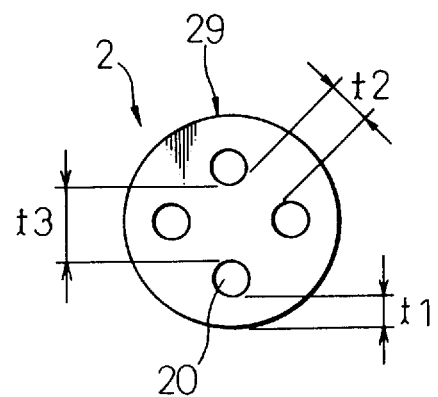
FIG. 3 is a transverse cross sectional view of the seal member in FIG. 2.

As shown in FIG. 2, the elastic seal member 2 is essentially of a cylindrical shape having axially opposite end surfaces 2-1, to which ends of the holes 20 are opened. In FIG. 3, in a plane transverse to the axis of the elongation of the electric seal member 2, $t_2$ is the minimum thickness of the member 2 between the holes 20 which are adjacent with each other, while $t_1$ is the minimum thickness of the member 2 between the hole 20 and an outer surface of the member 2. According to the present invention, values of the thickness $t_2$ and $t_1$ are 1 mm or more. Furthermore, in this embodiment, the outer cover 12 together with the inner cover 13 are subjected to an inwardly directed crimping operation, so that the elastic seal member 2 is displaced inwardly so that a deformation of in a range between 10 to 20% is obtained at the diameter of the member 2.

The detecting element 3 (FIG. 1) is of an elongated cup shape and is made of a solid electrolyte material such as a zirconia. The detecting element 3 is connected to a housing 4 in a fluid tight manner. Namely, the housing 4 has an upper flange portion 4-1 defining a stepped recess at it upper end. The detecting member 3 has a flange portion 3-1, which rests on the stepped recess. Then, a seal material 24 made of a talc is first filled and then a seal pad 26 and an insulator 27 are attached to the housing 4, so that the fluid tight connection of the detecting element 3 to the housing 4 is obtained.

In a known manner, the detecting element 3 is formed therein with an axially elongated air chamber 28 having an inner surface on which an inner electrode 30 is formed so that the inner electrode 30 is contacted with the reference air in the air chamber 28. An outer perforated cover 31 made of a metal material is, at its top end, fixedly connected to a bottom end of the housing 4. An inner perforated cover 32 is arranged inside the outer perforated cover 31 so as to cover the end of the detecting element 3. A detection chamber 29 is formed inside the cover 32, so that the detecting element 3 contacts the exhaust gas in the detection chamber 29. Also in a known manner, the detecting element 3 is formed with an outer surface, on which an outer electrode 33 is formed, so that the outer electrode 33 contacts with the gas to be measured in the detecting gas chamber.

The bottom cover 11 of a tubular shape is, at its lower end, sealingly connected to a top end of the housing 4 via a metal ring 35. The inner cover 13 is inserted to the bottom cover 11 and is fixed thereto by means of a crimping at circumferentially spaced portions 13-1, while the rigid insulator sleeve 15 is arranged between top end of the bottom cover 11 and a shoulder portion 13-2 of the inner cover 13. The outer cover 12 constructed by a first (upper) section 12A and a second (lower) section 12B is inserted to the inner cover 13 until the bottom end of the outer cover 12 abuts the shoulder portion 13-2 of the inner cover 13, so that the covers 12 and 13 are fixedly connected with each other by crimping the first section 12A of the cover 12 at location 12A-1, while a water repellent filter member 36 of a tubular shape is arranged between the covers 12 and 13. In other words, crimping of the second section 12B of the cover 12 at the positions 12B-1 causes the water repellent filter member 36 to be deformed and to be held between the covers 12 and 13. In short, at the first section 12A, the outer cover 12 is in a direct contact with the inner cover 13, i.e., no filter exists between the covers 12 and 13, while, at the second section 12B, the filter 36 is arranged between the covers 12 and 13.

Holders 40 and 42 are connected to the detecting element 3 so that they are in an electric connection with the outside and inside electrodes 33 and 30, respectively. Extending axially from the holders 40 and 42 are outlet lead wires 44 and 46, respectively. The insulator 15 is formed therein with holes 47, to which the lead wires 44 and 46 are introduced from the bottom of the insulator 15. Terminal members 48 and 50 are introduced into the holes 47 in the insulator 15 from the top thereof, where the terminal members 48 and 50 connected to the lead wires 44 and 46. Finally, the lead wires 16 and 18 passed through the elastic seal member 2 are connected to the terminal members 48 and 50, respectively. In short, an electric connection of the lead wires 16 and 18 to the outside and the inside electrode 33 and 30 are, thus, created.

The heater 5 is arranged inside the air chamber 28 and has an upper end 5-1 extended therefrom. An electrode 54 is formed on the upper end 5-1 of the heater 5, and is connected to a fine lead wire 55. The lead wire 55 is electrically connected to a terminal 56 in the hole 47 in the insulator 15. The lead wire 19 passed through the elastic seal member 2 is electrically connected to the terminal 56. In short, an electric connection of the lead wire 19 to the electrode 54 of the heater 5 is thus obtained.

The elastic seal member 2 is, as shown in a perspective view in FIG. 2, formed with four of the lead wire holes 20. Two of the holes 20 are for introducing the lead wires 16 and 18 to the detecting element 3. The remaining two holes 20 are for introducing the lead wires 19 to the heater 5. In FIG. 3, between the minimum thickness $t_2$ of the elastic seal member 2 between the holes 20 and the minimum thickness $t_1$ of the elastic seal member 2 between the hole 20 and the outer surface of the member 2, a relationship is obtained that $t_1 < t_2$. In other words, $t_1$ constructs the minimum thickness of the elastic seal member 2. Furthermore, $t_3$ in FIG. 3 shows a thickness of the elastic member between the inner surfaces of the holes which are diametrically spaced and is larger than the minimum thickness $t_1$.

According to the this embodiment of the air fuel ratio sensor, both of the minimum thickness $t_2$ between the holes 20 which are adjacent with each other and the minimum thickness $t_1$ between the hole 20 and the outer surface 29 are larger than 1 mm. Furthermore, the cover 12 is, at position 12A-1 in its first section 12A, subjected to a crimping in such a manner that a deformation of the elastic seal member 2 is occurred in a range between 10 to 20% of the outer diameter of the member 2. As a result, a compression force in a desired range is generated in the elastic member 2, so that a reduction of a compression force is obtained at the portions of the elastic member 2 of the reduced thickness $t_1$ or $t_2$, while obtaining a desired sealing effect of the lead wires 16, 18 and 19 in the respective holes 20. Thus, in a situation of an exposure to water, water can be effectively prevented from being introduced into a space inside the sensor.

Furthermore, in this embodiment, the elastic sealing member 2 allows a desired watertight performance even in an atmosphere at a high temperature. Thus, the construction of the air fuel ratio sensor according to this embodiments allows the sensor to be located in an area of high temperature which was impossible for the prior art structure.

Now, a relationship between the service life as related to a waterproofness and the minimum thickness will be explained with reference to FIG. 4. A measurement of the service life as related to waterproofness is as follows. The air fuel ratio sensor, the output of which is connected to a recording device, is arranged in a pipe through which a combustion gas as generated by a combustion of a rich air fuel mixture is passed, so that the detecting element is subjected to the combustion gas of a temperature higher than the activated temperature of the detecting element, while a desired temperature of the elastic insulating member 2, which is 240° C. for the elastic insulating element 2 based on a fluorine, is maintained. The output of the air fuel ratio sensor is connected to a recorder, while the air fuel ratio sensor is subjected to a periodic spray of a flow of water. An observation of the detected signal from the sensor recorded on the recorder is done in order to determine if a significant reduction occurred in the output level in the detected signal.

Figure 1:
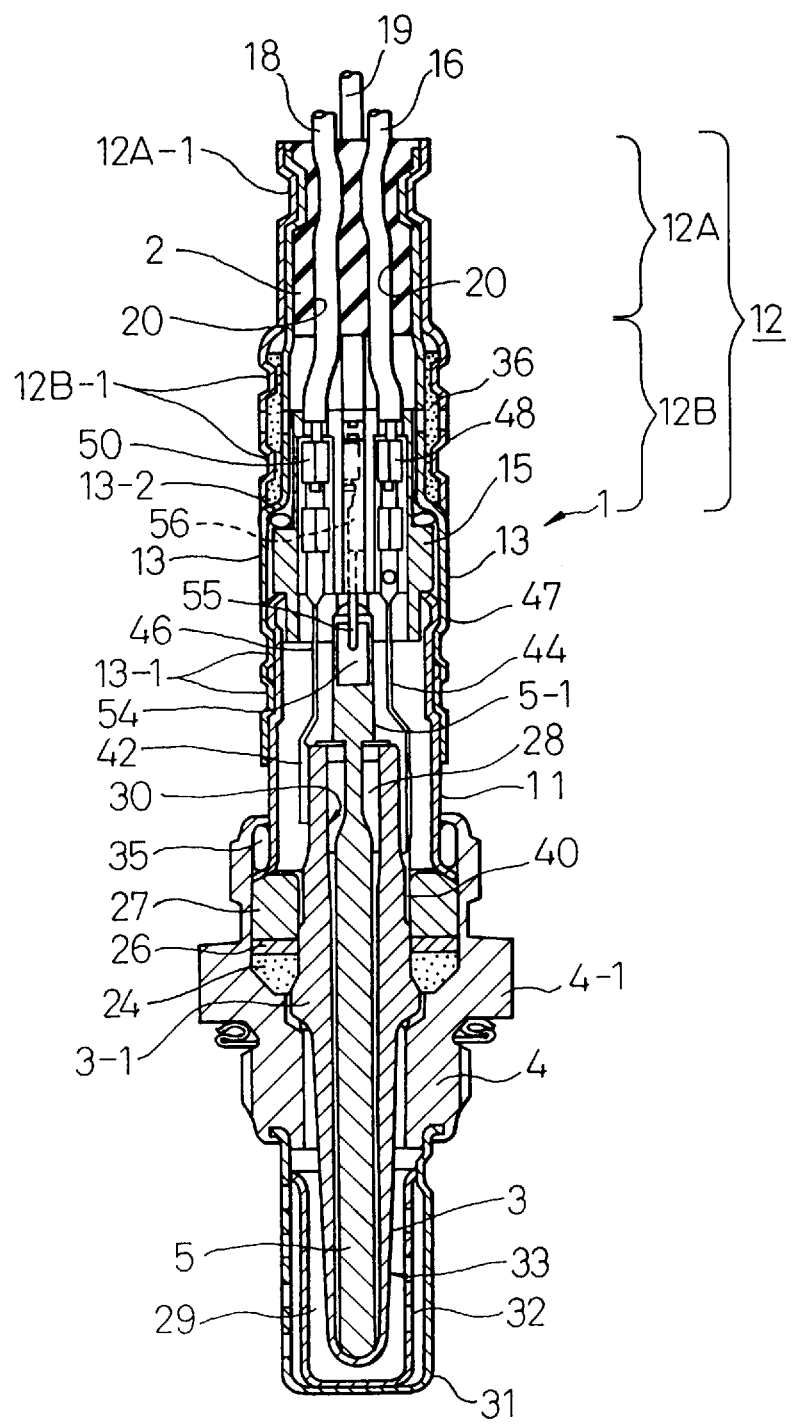
FIG. 1 is a longitudinal cross sectional view of an air fuel ratio sensor according to the present invention.

The measurement was done by using the air fuel ratio sensor as shown in FIG. 1 provided with the elastic insulating member 2 as shown in FIGS. 2 and 3, wherein the covers 12 and 13 are crimped at the position 12A-1 as shown in FIG. 1 for causing the elastic insulating member 2 to de deformed. Four samples of the air fuel ratio sensor of different values of degree of the deformation with respect to its outer diameter, that are 5, 10, 15 and 20%, respectively, were prepared. For each of sensors of different values of the degree of the deformation, three samples of different values of the minimum thickness ($t_2$ in FIG. 3) 0.5, 1.0 and 1.5 mm were prepared.

Figure 4:
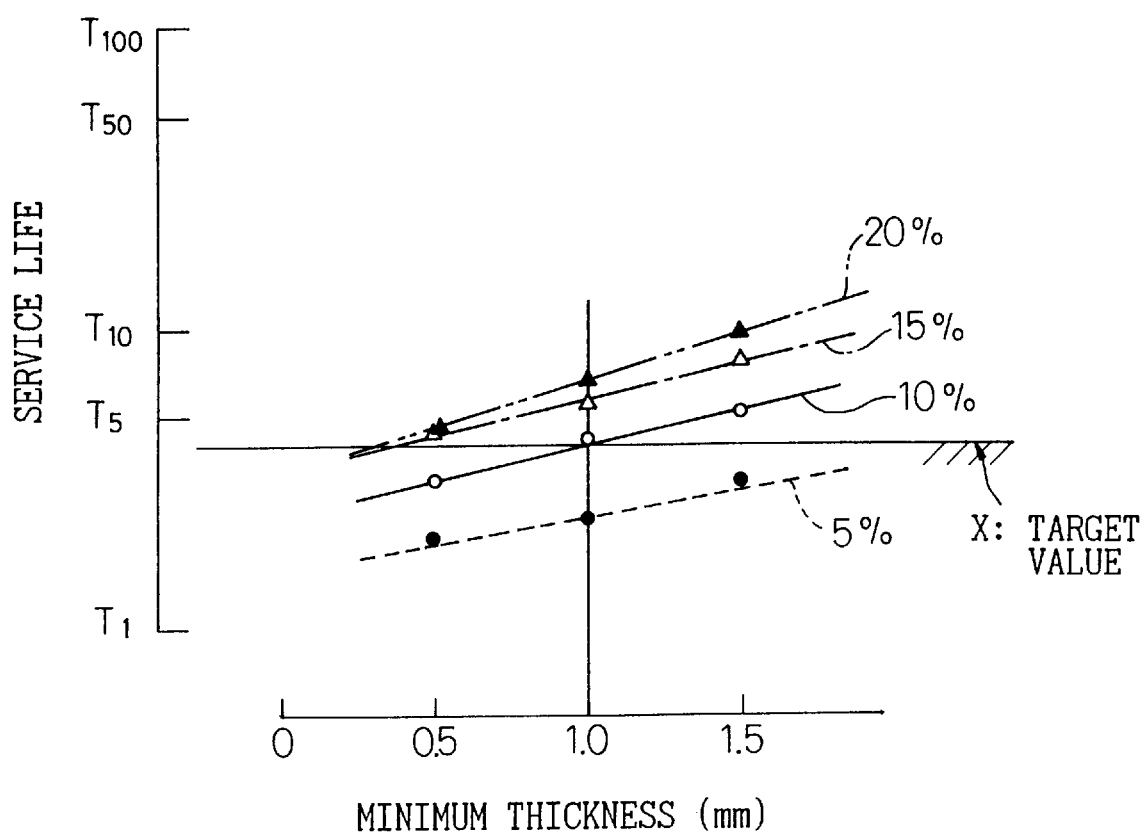
FIG. 4 is graphs showing relationships between the minimum thickness and the waterproofness in terms of service life.

In FIG. 4 showing the relationship between the minimum thickness and the service life under the water spray test, a level X shows a target value of the service life, which is requested by a user side, such as an automobile on which the air fuel sensor according to the present invention is to be mounted. As will be understood from FIG. 4, the sample of the value of the degree of deformation in a range between 10 to 20% can provide values of service life larger than the target value (X) so long as the minimum thickness is 1.0 mm or larger. Contrary to this, the minimum thickness smaller than 1.0 mm or the degree of the deformation smaller than 10% causes the service life to be reduced below the target value X, causing the waterproofness to be insufficient.

Figure 5:
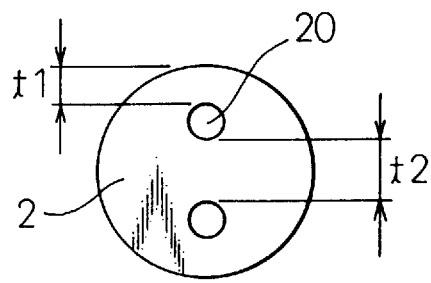
FIGS. 5 to 7 are transverse cross sectional views of the seal member in respective modifications.

As a modification, the number of the holes 20 of the elastic insulating member 2 can be other than four as is the case in the embodiments in FIGS. 1 to 4. Namely, in FIG. 5, the member 2 is formed with two of the holes 20. In this modification, $t_1$ is the minimum thickness between the inner surface of the hole 20 and $t_2$ is the minimum thickness between the holes 20. In this case, $t_2 > t_1$, and thus $t_1$ is the minimum thickness of the material in the elastic member 2 in FIG. 5.

Figure 6:
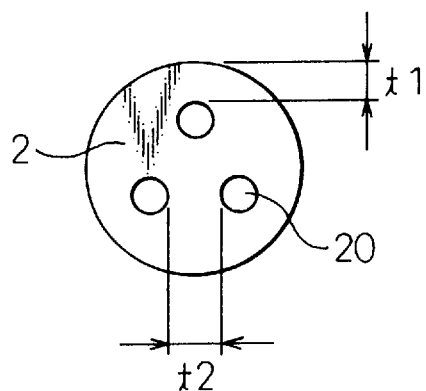

In a modification in FIG. 6, the elastic member 2 is formed with three of the lead wire passage holes 20. In this case, $t_2$ is the minimum thickness of the material between the holes, and $t_1$ is the minimum thickness between the hole 20 and the outer surface of the member 2 and is smaller than $t_2$. Thus, $t_1$ becomes the minimum thickness of the seal member 2.

Figure 7:
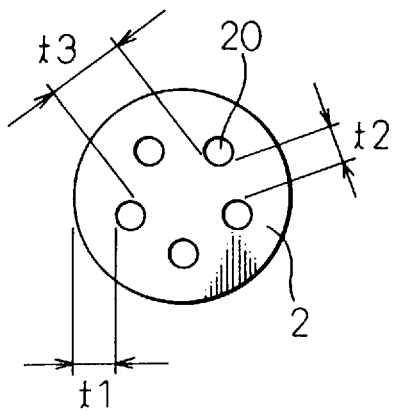

In a modification in FIG. 7, the elastic member 2 is formed with five of the holes 20. In FIG. 7, $t_2$ is the minimum thickness between the holes 20 which are adjacent to each other, $t_1$ is the minimum thickness between the hole 20 and the outer surface of the member 2 and is smaller than $t_2$, and $t_3$ is the minimum thickness of between the holes 20 which are spaced with each other. In this case, $t1 < t2 < t3$. Thus, $t_1$ is the minimum thickness.

In FIG. 8A showing an enlarged partial cross sectional view at the crimped section 12A of the outer cover 12, the hole 20 is, at its inner surface, formed with ribs 21 as projected radially inwardly, while forming a rounded cross section. The ribs 21 extend circumferentially so as to form two longitudinal spaced rings. In place of the ribs of the rounded cross sectional view, ribs 21' of a triangular cross sectional view as shown in FIG. 9A, extending circumferentially so as to form longitudinally spaced three rings are formed.

FIGS. 8A and 9A show state of the seal members 2 before introduction of the lead wire 16, 18 or 19. In this case gaps 120 exist between the covers and seal members. The lead wires are inserted to the respective opening 20 and the covers are subjected to crimping. In this case, a force directed radially inwardly is generated in the covers, so that the ribs 21 are brought into a contact with the lead wires, while being easily deformed, resulting in a positive and reliable seal between the lead wires and the holes. Thus, an increased waterproofness is realized in the sensor according to the present invention.

Furthermore, the crimping of the outer cover is done at a location where the ribs are provided. Thus, even in a case where a difference of the inner diameter of the hole with respect to the outer diameter of the lead wire does not cause the ribs to be subjected to a deformation by a mere pressure insert of the lead wires, a positive deformation of the ribs is obtained. Thus, a desired seal is maintained between the lead wires and the corresponding holes.

The construction in FIGS. 8A and 8B and 9A and 9B is desirable in that a precision of the lead wires and the holes 20 are less important. Furthermore, a tolerance is increased as to the dimension of the lead wires and holes, which makes the process of assembly easy.

FIG. 10 shows a air fuel ratio sensor in a different embodiment. As similar to the embodiment in FIG. 1, the sensor 1 includes a housing 4 and a detecting element 3 which is inserted to the housing 4. A cover assembly for inserting lead wires 16, 18 and 19 is arranged above the cover assembly, which is constructed by an outer cover 12 and an inner cover 13. In this embodiment, the bottom cover 11 in FIG. 1 is eliminated and the inner cover 13 is directly connected to the housing 4 via the metal ring 35. The inner cover 13 has an upper portion 13B of a reduced diameter over the remaining portion 13A. A water repellent filter member 36 is arranged between the outer cover 12 and the reduced diameter portion 13B of the inner cover 13.

In FIG. 10, the outer cover 12 is inserted to the inner cover 13 and has a first section 12A, which is in contact with the inner cover 13, i.e., no water repellent filter 36 exist between the covers 12 and 13 and a second section 12B which are spaced from the inner cover 13, i.e., the water repellent filter 36 exists between the covers 12 and 13. In order to fixedly connect the outer cover 12 to the inner cover 13, the outer cover 12 is subjected to a crimping at positions 12A-1 in the first section 12A. Furthermore, the outer cover 12 is subjected to a crimping at positions 12B-1 in the second section 12B, which allows the water repellent filter 36 to be fixed between the inner and outer covers 12 and 13.

It should be appreciated that, in the arrangement in FIG. 10, the first section 12A is located nearer to the housing 4 than the second section 12B, i.e., the first section 12A is located below the second section 12B. It should further be appreciated that the outer cover 12 has, at the first section 12A, an outer diameter which is identical to that at the second section 12B.

In FIG. 10, the outer cover 12 is, at its top end, formed with a tubular section (third section) 12C of a reduced diameter opened upwardly, so that the outer cover 12 forms a shoulder portion 12D at a bottom of the tubular section 12C. The rigid, ceramic insulator 15 is fitted to the inner cover 13 from its top end, until a flange portion 15A is contacted with the top end surface of the cover 13 via a disk shaped spring 60, while the elastic seal member 2 made of a rubber material is sealingly inserted to an opening 62 of the tubular section 12C of the outer cover 12. The outer cover 12 is subjected to crimping at a position 12C-2 in the tubular section 12C, which causes the elastic seal member 2 to be deformed, which allows the member 2 to be fixedly connected to the outer cover 12, while obtaining a fluid tight connection not only between the cover 12 and the seal member 2 but also between the seal member 2 and the lead wires 16, 18 and 19.

These outer and inner covers 12 and 13 are made of a stainless steel based on an austenite such as SUS304LCP. Furthermore, the outer cover 12 has a hardness Hv of a value of about 150 and a thickness of a value about 0.5 mm, while the inner cover 13 has a hardness Hv of a value of about 240 and a thickness of a value about 0.7 mm.

As in the embodiment in FIG. 1, the detecting element 3 has layers of outer and inner electrodes 30 and 33, which are in electrical connection with the holders 40 and 42, the lead wires 44 and 46, the terminals 48 and 50, and the lead wires 16 and 18, respectively, while the heater 5 is in electrical connection with the lead wire 55, the terminals 56 and the lead wires 19. As in the embodiment in FIG. 1, the connection terminals 48, 50 and 56 are passed through respective holes in the insulator 15 fitted to the inner cover 13, and are passed through respective holes in the elastic seal member 2 fitted to the opening 62 in the tubular section 12C.

In FIG. 10, the outer and inner covers 12 and 13 are formed with lateral openings 64 and 66 for an air ventilation, between which the water repellent filter 36 is located. Due to an outwardly opened porous structure of the water repellent filter 36, a desired ventilation effect of the air chamber 28 in the sensor 1 is obtained by an assistance of a gap between the outer cover 12 and the filter 36. As an alternative, a gap is provided between the inner cover 13 and the water repellent filter 36.

Now, a construction of an apparatus 68 for obtaining the above structure of the crimping the outer cover 12 will now be explained. Namely, in FIG. 11, the apparatus for caring out the crimping is constructed by a body 70 as an annular member, a first set of eight circumferentially spaced pressers 72 of a substantially sector shape for executing a crimping of the first section 12A of the inner cover 12 at the locations 12A-1, a second set of pressers (not shown) spaced axially from the first set of the pressers for executing a crimping of the second section 12B of the inner cover 12 at the locations 12B-1, and a third set of pressers (not shown) spaced axially further from the first set of the pressers for executing a crimping of the top portion 12C at the locations 12C-2. The pressers 72 have an arc shaped inner working end 72A, which cooperates to form a substantially complete circle at the crimped position of the pressers 72. Thus, an even crimping along the entire circumference of the cover is obtained.

During the operation of the apparatus in FIG. 11, the body 70 is, first, located on a longitudinal position, where the pressers 70 in the first set are initially located radially outwardly as shown by a phantom line and then are moved radially inwardly toward position as shown by solid lines, which causes the outer cover 12 to be displaced radially inwardly, thereby crimping the first section 12A at the positions 12A-1. Then, the second set of the pressers are operated in a similar manner, thereby crimping the second section 123 at the positions 12B-1. Finally, the third set of the pressers are operated, thereby crimping the tubular (third) section 12C at the positions 12C-2.

It should be noted that, prior to the crimping operation, the sensor assembly 1 is placed substantially horizontally in a support stand (not shown) having an opening for receiving the sensor 1, which allows the crimping operation to be executed at the first, second and third sections 12A, 12B and 12C. The crimping at the first section 12A by the radially inwardly movement of the first set of the pressers 72 allows the outer cover 12 to be fixedly connected to the inner cover 13. The crimping at the second section 12B by the radially inwardly movement of the second set of the pressers allows the water repellent filter 36 to be fixedly arranged between the outer and inner covers 12 and 13. Finally, the crimping at the third section 12C by the third set of pressers allows the rubber seal member 2 to be fixedly connected to the outer cover 12.

In the construction of the air fuel ratio sensor 1 in FIG. 10, the crimping of the outer cover 12 to the inner cover 13 is done at the first section 12A, which is in a direct contact with the inner cover 13. In other words, nothing exists between the crimped portions of the outer and inner covers 12 and 13, thereby obtaining a reliable connection of the outer cover 12 to the inner cover 13 by the crimping. Furthermore, the crimped portion of the inner cover 12 is located not at its top end but at an intermediate portion adjacent the housing 4, where the inner cover 13 has an increased diameter, resulting in an increased strength of the connection of the outer cover 12 to the inner cover 13. In short, according to this embodiment of the present invention, a reliable connection between the outer and inner covers 12 and 13 is obtained, which is enough to obtain a desired strength of the connection with respect to any vibration occurred in the air fuel ratio sensor during its use in an automobile, while maintaining a desired fluid seal between the crimped portion 12A-1.

In the construction of the air fuel ratio sensor in FIG. 10, the ceramic insulator 15 is fixedly connected between the shoulder portion 12D of the outer cover 12 and the end surface of the inner cover 13, thereby obtaining a reliable fixation of the insulator 15, which assists in a reliable electrical insulation of the lead wires 16, 18 and 19, thereby enhancing the performance as well as the reliability of the operation of the air fuel ratio sensor.

In the construction of the air fuel ratio sensor in FIG. 10, the diameter of the lower portion 13A opposite the first section 12A of the outer cover 12 is larger than the diameter of the upper portion 13B opposite the second section 12B. This construction assists in obtaining an increased durability to a vibration.

In the construction of the air fuel ratio sensor in FIG. 10, the rubber seal 2 is fitted to the top opening 62 of the outer cover 12. As a result, an increased sealing is obtained at a location where the cover 12 is faced with the seal 2, thereby preventing water from entering into the space inside the air fuel ratio sensor 1.

Finally, in the embodiment in FIG. 10, the inner cover 13 has a value of hardness larger than that of the outer cover 12, which assists in increasing a reliability of fixing, to the inner cover, of the outer cover 12 at the first section 12A.

FIG. 12 shows a modification, which, in place of a combination of the insulator 15 and the disk shaped spring 60, a spacer 74 made of a resin material is arranged between the shoulder portion 12D of the outer cover 12 and a top end of the inner cover 13. The spacer 74 is formed with holes, through which lead wires 16, 18 and 19 from the detecting element 3 and the heater 3 pass. The remaining construction is the same as that in FIG. 10, and thus a detailed explanation thereof will be omitted.

In an air fuel ratio sensor in FIG. 13, an inner cover 13 is provided which is constructed by a lower section 13A connected to the housing 4 via the seal member 24 and the metal ring 35, a middle section 13B of a diameter smaller than that of the lower section 13A and a upper section 13C of a diameter smaller than that of the medium portion 13B. An outer cover 12 is provided which is constructed by a lower (second) section 12B and an upper (first) section 12A of a diameter smaller than that of the second section 12B. Furthermore, the water repellent filter 36 is arranged between the second section 12B of the upper cover 12 and the intermediate section 13B of the lower cover 13 and is held there between by crimping the second section 12B at the locations 12B-1. The first section 12A of the outer cover 12 is under direct contact with the section 13C of the inner cover 13. Furthermore, the first section 12A is connected to the section 13C by crimping the section 12A at the location 12A-1 without interposing the filter therebetween.

It should be appreciated that the strength of the crimping at the first section 12A is larger than the strength of the crimping at the second section 12B. Furthermore, as will be explained later, the process for crimping of the outer cover 12 is such that the crimping at the first section 12A is completed simultaneously or prior to the completion of the crimping at the second section 12B, and that the crimping at the first section 12A is commenced prior to commencing the crimping of the second section 12B.

In the structure of the air fuel ratio sensor in FIG. 13, the inner cover 12 supports the upper cover 13 at the crimped portions 12A-1 at its first section 12A. Furthermore, fixing of the water repellent filter 36 between the outer and inner covers 12 and 13 is done by crimping the second section 12B of the cover 12 at the longitudinally spaced locations 12B-1.

The outer cover 12 is, at its second section 12B, formed with lateral openings 64, while the inner cover 13 is, at its middle section 13B, formed with lateral openings 66, which are opposite to the openings 64 via the water repellent filter 36. A gap 67 is formed between the outer cover 13 and the filter 36 so that the openings 64 are opened to the gap 67. Thus, the openings 64 and 66 and the gap construct a passage for introducing an air into the space inside the sensor. The porous nature of the filter 36 prevent the air flow from being blocked.

In the embodiment in FIG. 13, the outer and inner covers 12 and 13 are also made of a stainless steel based on an austenite such as SUS304LCP. Furthermore, the outer cover 12 has a hardness Hv of a value of about 150 and a thickness of a value about 0.5 mm, while the inner cover 13 has a hardness Hv of a value of about 240 and a thickness of a value about 0.6 mm.

In the structure of the air fuel ratio sensor in FIG. 13, a holder 76 is inserted to the upper end of the housing 4. The detecting element 3 is inserted to a central hole in the holder 76 and a glass seal 78 is filled and a spacer 80 is fitted so that the detecting element 3 is held by the holder 76. The detecting element 3 is formed of a plate as a laminated structure in which an electric heater (not shown) is buried. The detecting element 3 is, at its outer surface, formed with a detecting portion 3A, which is in contact with a gas in the reference gas chamber 29 inside the double structure of the outer and inner perforated covers 31 and 32. These detecting portion 3A extends to lead wires 44 and 46 at the top of the detecting element 3, while the electric heater extends to lead wires 55. The lead wires 44 and 46 from the detecting portion 3A are the lead wires from the heater are via terminals 48 and 50 et al, connected to the lead wires 16 and 18 and 19, respectively, in a similar way to that in FIG. 1.

In the construction in FIG. 13, the ceramic insulator 15 is arranged movably in the inner cover 13, while a coil spring 80 is arranged in the cover 13 for generating a spring force which urges the insulator 15 to move downwardly until the insulator 15 abuts, at its bottom end, the top end of the holder 76. In the similar manner as that in FIG. 1, the insulator 15 forms holes through which the terminals 48 and 50 are inserted.

The rubber (elastic) seal (bushing) 2 is fitted to the section 13C of the inner cover 13. The crimping at the portion 12B-1 causes the first section 12A to be fixed to the inner cover 13 and causes the rubber seal 2 to be deformed.

Now, an apparatus 68 for crimping the outer cover in FIG. 13 will be explained with reference to FIGS. 14 and 15. The apparatus 68 includes a body 70 as an annular member, a first part 72 including a set of eight circumferentially spaced pressers 72-1 of a substantially sector shape for executing a crimping of the first section 12A of the inner cover 12 at the locations 12A-1, and a second part 73 axially spaced from the first part 72 and including two axially spaced sets, each having eight circumferentially spaced of pressers 73-1 for executing a crimping of the second section 12B of the outer cover 13 at locations 12B-1. In FIG. 15, each of these pressers 72-1 and 73-1 is radially slidable with respect to the body between an outward position as shown by a phantom line in FIG. 13 to a position as shown by a sol id line. The pressers 72-1 in the part 72 are connected to a corresponding actuator for generating their radial reciprocating movement. The presser 73-1 in the part 73 are connected to a corresponding actuator for generating their radial movement. Furthermore, the crimping apparatus 68 is further provided with a work holder 82, which forms a lateral bore 82-1 for holding the sensor during the crimping operation.

During the operation of the apparatus in FIG. 14, the sensor 1 is inserted to the bore 82-1 so that the sensor 1 is held horizontally, while the part of the outer cover 12 is located outwardly. Then, the crimping apparatus 68 is arranged such that the cylindrical body 70 is located around the outer cover 12 and the pressers 72-1 and 73-1 take initial position where they are located radially outwardly as shown by a phantom line FIG. 15. The first pressers 72-1 are, first, moved radially inwardly toward a position as shown by solid lines, which causes the first section 12A of the outer cover 12 to be displaced radially inwardly at the location 12A-1, thereby connecting the outer cover 12 to the inner cover 13. Then, the second pressers 73-1 are moved radially inwardly, thereby crimping the second section 12B of the outer cover 12 to be displaced radially inwardly at the positions 12B-1, which allows the water repellent filter 36 to be held between the covers 12 and 13.

After the completion of the crimping operation, the first pressers 72-1 are, first, moved away from the first section 12A of the outer cover 12. Then, the second pressers 73-1 are moved away from the second section 12B of the outer cover 12, thereby finishing an assembling of the water repellent filter in the sensor 1.

In the crimping apparatus in FIGS. 14 and 15, it is desirable that, during the crimping operation, the body of the sensor 1 is fixed axially by the bore 82-1 of the holder 80 by suitable means, which allows the outer cover 12 allows the cover 12 to be positively hold to the body of the sensor.

During the operation of the crimping apparatus in FIG. 14, the crimping of the first section 12A is completed prior to the completion of the crimping of the second section 12B. Namely, according to the present invention, the first section 12A of an increased value of a required crimping force is first fixed, and then the second section 12B is subjected to a crimping at a force smaller than that at the first section 12A, so that the crimped strength at the second section 12B is smaller than that at the first section. As a result, the initially crimped portion 12A is prevented from being influenced by the force generated at the crimping of the second section 12B. In other words, a relative displacement between the outer and inner covers 12 and 13 is prevented during the crimping operation. Thus, a secure connected condition by the crimping is obtained between the outer and inner covers 12 and 13 and the water repellent seal 36, resulting in a reliably sealed condition at these parts.

Furthermore, in the method according to the embodiment in FIG. 14, the first section 12A with no provision of the water repellent filter is subjected to the initial stage crimping, which allows the outer and inner covers 12 and 13 to maintain their axially aligned condition prior to the crimping at the second section 12B with the water repellent filter 36. Thus, a circumferentially even radial gap between the covers 12 and 13 is obtained when the crimping at the first section 12A is finished. Then, the second stage crimping is done at the second section 12B, which allows the filter 36 to be subjected to an even deformation of the filter 36, while being fixed between the outer and inner covers 12 and 13. In other words, a concentric arrangement is obtained between the outer and inner covers 12 and 13 as shown in FIG. 16A. Otherwise, a relative displacement would occur between the outer and inner covers 12 and 13, resulting in a circumferentially uneven deformation of the filter as show in FIG. 16B. In short, a easy and a reliable assembly of the water repellent filter 36 is attained according to this embodiment of the present invention.

In the execution of the crimping according to the present invention, no separate part, such as a rubber sheet is used between the water repellent filter 36 and the outer cover 12 is used, which is advantageous in a reduced number of parts and in reduced work during assembly of the sensor.

FIG. 17 shows a modified embodiment of the crimper apparatus, wherein the first presser 72-1 for crimping the first section 12A of the outer cover 12 and the second pressers 73-1 for crimping the second section 12B of the outer cover 12 are connected integrally to a body of the sector 84. The pressers 72-1 for crimping the first section 12A are located radially inwardly over the presser 73-1 for crimping the second section 12B in such a manner that the crimping of the first section 12A is done first. Namely, a radial movement of the sectors 84 causes the pressers 72-1 to be contacted with the first section 12A of the outer cover at the locations 12A-1, so that the crimping of the section 12A is, first, initiated. The radial movement is continued so that the pressers 73-1 are also brought to a contact with the second section 12B at the locations 12B-1. The radial movement of the sectors 84 is stopped when a predetermined stroke is obtained, thereby finishing simultaneously the crimping of the first section 12A at an increased crimping force and the crimping of the second section 12B at a reduced crimping force.

FIG. 18 shows a modification where the top section 13C of the inner cover in FIG. 13 is eliminated, while the outer cover 12 includes, in addition the sections 12A and 12B, a further section 12C, which is the top extension of the outer cover 12. Namely, the section 13C extends upwardly from the second (intermediate) section 12B. In this embodiment in FIG. 18, as similar to the embodiment in FIG. 13, the crimping at the first section 13A with no seal is, first, done at positions 12A-1 at larger crimping force, which is followed by a crimping at the second section 12B with the seal 36 at positions 12B-1. Finally, crimping at the section 12C is done at position 12C-1 for fixing the rubber seal member 2.

In another embodiment in FIGS. 19 and 20, the air fuel ratio sensor is provided with a separate lower cover 11 as also used in the first embodiment in FIG. 1. The base cover 11 is connected to the housing 4 via a metal ring 35 by crimping the top edge of the housing 4-1. The inner cover 13 is, at its bottom end, inserted to the top end of the lower cover 79 and connected thereby by crimping the inner cover 13 at location 13C-1. In the similar way, the outer cover 12 includes the lower (second) section 12B with the water repellent filter 36 and the upper (first) section 12A with no intervention of such a water repellent filter. Furthermore, the outer cover 12 is firmly connected to the inner cover 13 by crimping the first section 12A with no filter at the location 12A-1, while the filter 36 is sandwiched between the outer and inner covers 12 and 13 by crimping the second section 12B at the locations 12B-1.

In the similar manner, the crimping at the first section 12A is first done at an increased crimping force, which is followed by a crimping at the second section 12B at a reduced force.

In FIG. 19, the sensor is provided with a holder 86 which is fixedly connected to the housing 4 by means of a packing 87, a talc seal 24, a pad and an insulator, while the detecting element 3 extends out of the housing 4.

In the structure in FIG. 19, the ceramic insulator 15 is arranged in the inner cover 13. A dish spring 80 is arranged between the axial faced ends surfaces of the lower cover 79 and the insulator 15, so that the spring urges the insulator 15 upward until its top end abuts a flange of the inner cover. Inside the insulator 15, the terminals 48 and 50 are inserted, from which the wires 44 and 48 extend downward, which are in connection with the respective electrodes of the detecting element 3. Furthermore, from the terminals 48 and 50, lead wires 16 and 18 are extended, which are passed through the elastic seal 2, which is firmly held by the inner cover 13 by crimping the outer over 12 at the location 12B-1.

The rest of the construction is the same as that in the preceding embodiments. Furthermore, the desired crimping operation is executed by using the crimping apparatus as explained with reference to FIG. 14.

FIG. 20 illustrates a process for assembling the sensor in FIG. 19. Namely, an upper part 88A is assembled from the inner cover 13, the outer cover 12, the insulator 15, the elastic seal 2, the water repellent filter 36, terminals 48 and 50, and the lead wires 44 and 46. In the upper assembly 88A, a first stage crimping at a larger force done at the first section 12A with no filter between the covers 12 and 13, which is followed by a second stage crimping of a reduced force at the second section 12B while the filter 36 is arranged between the covers 12 and 13.

On the other hand, separate from the upper part, a lower part 88B is assembled from the detecting element 3, the housing 4, the perforated sensor covers 31 and 32, the holder 86 and the lower cover 79 et al.

The separate lower cover 79 of the lower assembly 88B is inserted to the inner cover 13 of the upper assembly 88A, while the top end of the detecting element 3 of the lower assembly 88B is engaged with the elastic lead wires 44 and 46 of the upper assembly 88A. Then, a crimping of the section 13C of inner cover 13 is done at a location 13C-1 in FIG. 19, which causes the upper and the lower assemblies to be firmly connected with each other. This process of the assembly from the separate sub-assemblies in FIG. 20 is advantageous in that the labor productivity in the process of the assembly of the sensor is enhanced.

It should be noted in an application of a method for crimping according to the present invention to the sensor of a type having a detecting element 3 made of a cup shaped solid electrolyte as explained with reference to FIG. 1, the crimping of the outer cover 12 of a larger force is, first, done at the location 12A-1 in the upper section (first section) 12A with no filter, which is followed by the crimping of a smaller force at the locations 12B-1 in the lower section (second section) 12B with the water repellent filter 36.

In a modification in FIG. 21, the sensor 1 is of a type having a detecting element 3 made of a cup shaped solid electrolyte as explained with reference to FIG. 1. In this embodiment 1 the sensor 1 is different from the one in FIG. 1 in that the bottom cover 11 is eliminated, i.e., the inner cover 12 is, at its bottom end, connected to the housing 4, the inner cover 12 is terminated as a upper flange 12-1, which is in contact with an inner shoulder portion 13-3 of the outer cover 13, and the ceramic insulator 15 extends downwardly so that the latter is urged by a spring 80 to contact with an upper end of the insulator 27. The lead wires 18 and 19 et al are provided for an electrical connection to the detecting element 3 and the heater 5 is similarly provided.

In the embodiment in FIG. 21, the crimping of the outer cover 12 of a larger force is, first, done at the location 12A-1 in the lower section (first section) 12A with no filter, which is followed by the crimping of a smaller force at the locations 12B-1 in the upper section (second section) 12B with the water repellent filter 36.

FIG. 22 shows a sensor in a different embodiment, wherein an outer tube 90 made of a rubber material is provided, so that it extends to a space between an upper reduced diameter portion of the outer cover 12 and an upper reduced diameter portion of the inner covers 12 and 13. The outer repellent filter 36 is arranged between a lower increased diameter section of the upper cover 12 and a medium diameter section of the outer cover 13. Namely, in this embodiment, the outer cover 12 includes a first section (upper section 12A) with no intervention of the water repellent filter with reference to the inner cover 13 and a second section (lower section 12B) faced with the inner cover 13 by way of the water repellent filter 36 so that an air ventilation passageway is formed by the holes 64 and 66 in the covers 12 and 13, respectively and the gap between the outer cover 13 and the filter 36.

In the embodiment in FIG. 22, the lead wires 16, 18 and 19 et al from the detecting element (not shown) and the heater (not shown) are taken out via the elastic seal 2. The wires 16, 18 and 19 are passed through the space inside the tube 90 and are extended to a connector (not shown) at the other end of the tube 90.

During the crimping operation, prior to the connection of the outer cover 12 to the inner cover 13, the inner cover 13 is subjected to a crimping at locations 13-4, so that the rubber bushing 2 is subjected to a deformation, and thereby fixedly holds the bushing 2. Then, the end of the tube 90 is located between the upper end of the inner cover 12 and the lower end of the inner cover. Then, the outer cover 12 is subjected to a first stage crimping of a larger force at the locations 12A-1 in the upper section 12A of the cover 12, so that the outer cover 12 is connected to the inner cover via the tube 90. Finally, the outer cover 12 is subjected to a second stage crimping of a smaller force at the locations 12B-1, so that the water repellent filter 36 is held between the inner and outer covers 12 and 13.

In the instant embodiment, the employment of the rubber tube 90 allows the lead wires 16, 18 and 19 to be covered, thereby preventing them from being damaged by flying stones.

It should be noted that, in FIGS. 14 and 17, the covers 12 and 13 are illustrated at the state after the completion of the crimping process.

We claim:

1. An air fuel ratio sensor comprising:

a housing;

a detecting element arranged in said housing;

a cover assembly made of a metal material arranged on one end of the housing, said cover assembly comprising an inner cover and an outer cover located outwardly of the inner cover; and a water repellent filter arranged between said inner and outer covers;

said outer cover including a first section facing said inner cover without said water repellent filter intervening and a second section axially spaced from said first section and facing the inner cover via said water repellent filter;

said first section of the outer cover including first crimped portions causing the outer cover to be fixed with respect to the inner cover, said second section of the outer cover including second crimped portions causing the water repellent filter to be held between said inner and outer covers, said first section being located on one side of the second section adjacent to the housing.

2. A sensor according to claim 1, wherein said outer cover has, at said first section, an outer diameter larger than a diameter of the outer cover at said second section.

3. A sensor according to claim 1, further comprising a seal member made of an elastic material, which is fitted to an opening of the outer cover at an end remote from the housing, the outer cover having a crimped portion for causing the seal member to be scalingly fitted to the outer cover.

4. A sensor according to claim 1, wherein said inner cover has a hardness which is, at least at a portion opposing said first section of said outer cover, larger than hardness of the outer cover.

5. A sensor according to claim 4, wherein said inner and outer covers are made from a stainless steel and the said inner cover has a hardness Hv in a range between 150 and 400, while said outer cover has a value of hardness Hv in a range between 100 and 300.

6. A sensor according to claim 1, wherein said inner cover has a thickness larger than a sickness of said outer cover.

7. A sensor according to claim 1, wherein said inner cover outer covers are made from a stainless steel, the said inner cover has a value of hardness Hv in a range between 150 and 400, while said outer cover has a hardness Hv in a range between 100 and 300, the hardness of the inner cover being, at least at the first section, larger than a hardness of the outer cover, and the inner cover has a thickness in a range between 0.4 and 0.8 mm, said outer cover has a thickness in a range between 0.3 and 0.6 mm, the thickness of the inner cover being larger than a sickness of the outer cover.

8. A sensor according to claim 1, wherein eight of said crimped portions are provided at least at the first sections.

9. A sensor according to claim 8, wherein said eight crimped portions are evenly spaced along a circumference of the cover.

10. A method for assembling a gas sensor comprising the steps of:

providing a housing;

providing a detecting element for detecting a concentration of a gas to be detected and arranged in said housing and provided with terminals for taking out an output from the detecting element;

providing a cover assembly made of a metal material arranged on one end of the housing for storing therein the terminals, said assembly comprising an inner cover and an outer cover located outwardly of the inner cover;

providing an air permeable water repellant filter arranged between said inner and outer covers;

said outer cover including a first section to be arranged on said inner cover without intervening said water repellent filter and a second section axially spaced from said first section on the side and opposing the inner cover via said water repellent filter;

crimping said outer cover at said firstly section for causing the outer cover to be fixed with respect to the inner cover, and;

crimping said outer cover at second section for causing the water repellent filter to be held between said inner and outer covers;

the crimping at the first section being completed in relation to the crimping at the section such that the crimping at the first section is finished, at the latest, simultaneously with the finish of the crimping at the second section.

11. A method according to claim 10, wherein the crimping at the first section is finished prior to when the crimping at the second section is finished.

12. A method according to claim 10, wherein the crimping at the first section is commenced earlier than when the crimping at the second section is commenced.

13. A method according to claim 10, further comprising a step of holding the sensor horizontally during the crimping.

14. A method according to claim 10, further comprising the step of providing a rubber tube between the inner and outer covers at the first section.

15. A method according to claim 10, wherein the outer cover at the first section is in a direct contact with the inner cover.

16. A method according to claim 10, wherein the inner cover has a thickness larger than a thickness of the outer cover.

17. A method according to claim 10, wherein said inner and outer covers are made from a stainless steel and wherein the inner cover has, at least first section, a hardness Hv in a range between 150 and 400, while the outer cover has a hardness Hv in a range between 100 and 300, the hardness of the inner cover being larger than the hardness of the outer cover, and wherein the thickness of the inner cover is in a range between 0.4 and 0.8 mm, and the thickness of the outer cover is in a range between 0.3 and 0.6 mm.

18. A method according to claim 12, wherein the force of the crimping at the first section being larger than that at the second section.

19. A method according to claim 10 or 12, wherein said inner and outer covers are made from a stainless steel and wherein the inner cover has, at least at the first section, a hardness Hv in a range between 150 and 400, while the outer cover has a hardness Hv in a range between 100 and 300, while the hardness of the inner cover is larger than that of the outer cover.

20. A method according to claim 10 or 12, wherein it further comprises the step of providing a crimping device having a first set of pressers and a second set of pressers and wherein said crimping at the first section is performed by operating said first set of pressers, and the said crimping at the second section is performed by operating said second set of pressers.

21. A method according to claim 20, wherein the crimping of the first section by operating said first set of pressers is performed first, and wherein, upon completion of the crimping at the first section, the crimping of the second section is performed by operating said second set of pressers.

22. A method according to claim 20, wherein the crimping of the first section by operating said first set of pressers is commenced first and is followed by the commencement of crimping of the second section by operation said second set of pressers, and crimping at the first and second sections is completed simultaneously.

23. A method according to claim 10, wherein said first section is crimped at least at is done at eight circumferentially, evenly spaced locations.

24. A method according to claim 10, wherein at least at said first section, the inner cover has a hardness larger than a hardness of the outer cover.

* * * * *

UNITED STATES PATENT AND TRADEMARK OFFICE
CERTIFICATE OF CORRECTION

PATENT NO. : 5,874,664
DATED : February 23, 1999
INVENTOR(S) : WATANABE et al.

It is certified that error appears in the above-identified patent and that said Letters Patent is hereby corrected as shown below:

<u>Title page,</u>
Please change:
[75] Inventors: Isao Watanabe, Nagoya; Michihiro Yamakawa, Kariya; Masanori Fukutani, Nagoya; Toshihiro Sakawa, Toyohashi; all of Japan Signed and Sealed this Eighteenth Day of September, 2001

*Attest:*

*Nicholas P. Godici*

NICHOLAS P. GODICI
*Attesting Officer*     *Acting Director of the United States Patent and Trademark Office*